US007556813B2

(12) United States Patent
Bray et al.

(10) Patent No.: US 7,556,813 B2
(45) Date of Patent: Jul. 7, 2009

(54) ANTIVIRAL PEPTIDE-POLYMER CONJUGATE COMPRISING A POLYMER COVALENTLY ATTACHED TO TWO OR MORE SYNTHETIC HIV GP41 HR1 AND/OR HR2 PEPTIDES

(75) Inventors: Brian Bray, Graham, NC (US); Myung-Chol Kang, Langley, WA (US); Nicolai Tvermoes, Durham, NC (US); Daniel Kinder, Durham, NC (US); John William Lackey, Hillsborough, NC (US); Huyi Zhang, Durham, NC (US)

(73) Assignee: Trimeris, Inc., Durham, NC (US)

( * ) Notice: Subject to any disclaimer, the term of this patent is extended or adjusted under 35 U.S.C. 154(b) by 667 days.

(21) Appl. No.: 10/671,282

(22) Filed: Sep. 24, 2003

(65) Prior Publication Data

US 2004/0122214 A1 Jun. 24, 2004

Related U.S. Application Data

(60) Provisional application No. 60/414,439, filed on Sep. 27, 2002.

(51) Int. Cl.
*A61K 39/3085* (2006.01)
*A61K 39/21* (2006.01)

(52) U.S. Cl. .............................. 424/196.11; 424/208.1

(58) Field of Classification Search ............. 424/188.1, 424/208.1

See application file for complete search history.

(56) References Cited

U.S. PATENT DOCUMENTS 4,902,502 A * 2/1990 Nitecki et al. ............... 530/351
5,656,480 A 8/1997 Wild et al.
5,767,078 A 6/1998 Johnson et al.
6,113,906 A 9/2000 Greenwald et al.
6,258,774 B1 7/2001 Stein et al.
6,348,568 B1 2/2002 Barney et al.
6,573,078 B1 6/2003 Wild et al.

FOREIGN PATENT DOCUMENTS

WO WO 00/69902 * 11/2000

OTHER PUBLICATIONS

U.S. Appl. No. 09/350,641, filed Jul. 9, 1999, Barney et al.

* cited by examiner

*Primary Examiner*—Jeffrey S. Parkin
(74) *Attorney, Agent, or Firm*—Jones Day

(57) ABSTRACT

Provided are conjugates comprising a polymer having operably bound thereto no less than two molecules of synthetic peptide derived from HIV gp41; methods of using these conjugates to inhibit transmission of HIV to a target cell by adding an amount of effective to inhibit infection of the cell by the virus; and methods of producing the conjugates by operably binding each molecule of synthetic peptide, via a reactive functionality, to the polymer.

9 Claims, 6 Drawing Sheets

H-Tyr(tBu)-Thr(tBu)-Ser(tBu)-Leu-Ile-His(trt)-Ser(tBu)-Leu-Ile-Glu(OtBu)-
Glu(OtBu)-Ser(tBu)-Gln(trt)-Asn(trt)-Gln(trt)-Gln-Glu(OtBu)-Lys(Boc)-Asn(trt)-
Glu(OtBu)-Gln(trt)-Glu(OtBu)-Leu-Leu-Glu(OtBu)-Leu-Asp(tBu)-Lys(Boc)-Trp(Boc)-
Ala-Ser(tBu)-Leu-Trp(Boc)-Asn(trt)-Trp(Boc)-Phe-NH$_2$

1) HBTU, HOAT, DIEA, DMF
2) H$_2$O

1) TFA, DDT, H$_2$O
2) MTBE
3) Chromatographic Purification

SEQUENCE LISTING

```
<160> NUMBER OF SEQ ID NOS: 114

<210> SEQ ID NO 1
<211> LENGTH: 60
<212> TYPE: PRT
<213> ORGANISM: Human immunodeficiency virus

<400> SEQUENCE: 1

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp Gly Ile Lys Gln Leu Gln Ala Arg Ile Leu Ala Val
        35                  40                  45

Glu Arg Tyr Leu Lys Asp Gln Gln Leu Leu Gly Ile
    50                  55                  60

<210> SEQ ID NO 2
<211> LENGTH: 64
<212> TYPE: PRT
<213> ORGANISM: Human immunodeficiency virus

<400> SEQUENCE: 2

Trp Asn Ala Ser Trp Ser Asn Lys Ser Leu Glu Gln Ile Trp Asn Asn
1               5                   10                  15

Met Thr Trp Met Glu Trp Asp Arg Glu Ile Asn Asn Tyr Thr Ser Leu
            20                  25                  30

Ile His Ser Leu Ile Glu Glu Ser Gln Asn Gln Gln Glu Lys Asn Glu
        35                  40                  45

Gln Glu Leu Leu Glu Leu Asp Lys Trp Ala Ser Leu Trp Asn Trp Phe
    50                  55                  60

<210> SEQ ID NO 3
<211> LENGTH: 38
<212> TYPE: PRT
<213> ORGANISM: Artificial
<220> FEATURE:
<223> OTHER INFORMATION: synthesized

<400> SEQUENCE: 3

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln
        35

<210> SEQ ID NO 4
<211> LENGTH: 36
<212> TYPE: PRT
<213> ORGANISM: Artificial
<220> FEATURE:
<223> OTHER INFORMATION: synthesized
```

```
<400> SEQUENCE: 4

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 5
<211> LENGTH: 39
<212> TYPE: PRT
<213> ORGANISM: Artificial
<220> FEATURE:
<223> OTHER INFORMATION: synthesized

<400> SEQUENCE: 5

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 6
<211> LENGTH: 43
<212> TYPE: PRT
<213> ORGANISM: Artificial
<220> FEATURE:
<223> OTHER INFORMATION: synthesized

<400> SEQUENCE: 6

Gly Ser Thr Met Gly Ala Arg Ser Met Thr Leu Thr Val Gln Ala Arg
 1               5                  10                  15

Gln Leu Leu Ser Gly Ile Val Gln Gln Gln Asn Asn Leu Leu Arg Ala
            20                  25                  30

Ile Glu Ala Gln Gln His Leu Leu Gln Leu Thr
        35                  40

<210> SEQ ID NO 7
<211> LENGTH: 54
<212> TYPE: PRT
<213> ORGANISM: Artificial
<220> FEATURE:
<223> OTHER INFORMATION: synthesized

<400> SEQUENCE: 7

Gly Ser Thr Met Gly Ala Arg Ser Met Thr Leu Thr Val Gln Ala Arg
 1               5                  10                  15

Gln Leu Leu Ser Gly Ile Val Gln Gln Gln Asn Asn Leu Leu Arg Ala
            20                  25                  30

Ile Glu Ala Gln Gln His Leu Leu Gln Leu Thr Val Trp Gly Ile Lys
        35                  40                  45

Gln Leu Gln Ala Arg Ile
    50

<210> SEQ ID NO 8
<211> LENGTH: 36
<212> TYPE: PRT
<213> ORGANISM: Artificial
<220> FEATURE:
<223> OTHER INFORMATION: synthesized
```

<400> SEQUENCE: 8

Gly Ala Arg Ser Met Thr Leu Thr Val Gln Ala Arg Gln Leu Leu Ser
1               5                   10                  15

Gly Ile Val Gln Gln Gln Asn Asn Leu Leu Arg Ala Ile Glu Ala Gln
                20                  25                  30

Gln His Leu Leu
        35

<210> SEQ ID NO 9
<211> LENGTH: 38
<212> TYPE: PRT
<213> ORGANISM: Artificial
<220> FEATURE:
<223> OTHER INFORMATION: synthesized

<400> SEQUENCE: 9

Gly Ala Arg Ser Met Thr Leu Thr Val Gln Ala Arg Gln Leu Leu Ser
1               5                   10                  15

Gly Ile Val Gln Gln Gln Asn Asn Leu Leu Arg Ala Ile Glu Ala Gln
                20                  25                  30

Gln His Leu Leu Gln Leu
        35

<210> SEQ ID NO 10
<211> LENGTH: 40
<212> TYPE: PRT
<213> ORGANISM: Artificial
<220> FEATURE:
<223> OTHER INFORMATION: synthesized

<400> SEQUENCE: 10

Gly Ala Arg Ser Met Thr Leu Thr Val Gln Ala Arg Gln Leu Leu Ser
1               5                   10                  15

Gly Ile Val Gln Gln Gln Asn Asn Leu Leu Arg Ala Ile Glu Ala Gln
                20                  25                  30

Gln His Leu Leu Gln Leu Thr Val
        35                  40

<210> SEQ ID NO 11
<211> LENGTH: 50
<212> TYPE: PRT
<213> ORGANISM: Artificial
<220> FEATURE:
<223> OTHER INFORMATION: synthesized

<400> SEQUENCE: 11

Gly Ala Arg Ser Met Thr Leu Thr Val Gln Ala Arg Gln Leu Leu Ser
1               5                   10                  15

Gly Ile Val Gln Gln Gln Asn Asn Leu Leu Arg Ala Ile Glu Ala Gln
                20                  25                  30

Gln His Leu Leu Gln Leu Thr Val Trp Gly Ile Lys Gln Leu Gln Ala
        35                  40                  45

Arg Ile
    50

<210> SEQ ID NO 12
<211> LENGTH: 36
<212> TYPE: PRT
<213> ORGANISM: Artificial
<220> FEATURE:
<223> OTHER INFORMATION: synthesized

```
<400> SEQUENCE: 12

Ala Arg Ser Met Thr Leu Thr Val Gln Ala Arg Gln Leu Leu Ser Gly
1               5                   10                  15

Ile Val Gln Gln Gln Asn Asn Leu Leu Arg Ala Ile Glu Ala Gln Gln
                20                  25                  30

His Leu Leu Gln
        35

<210> SEQ ID NO 13
<211> LENGTH: 36
<212> TYPE: PRT
<213> ORGANISM: Artificial
<220> FEATURE:
<223> OTHER INFORMATION: synthesized

<400> SEQUENCE: 13

Arg Ser Met Thr Leu Thr Val Gln Ala Arg Gln Leu Leu Ser Gly Ile
1               5                   10                  15

Val Gln Gln Gln Asn Asn Leu Leu Arg Ala Ile Glu Ala Gln Gln His
                20                  25                  30

Leu Leu Gln Leu
        35

<210> SEQ ID NO 14
<211> LENGTH: 36
<212> TYPE: PRT
<213> ORGANISM: Artificial
<220> FEATURE:
<223> OTHER INFORMATION: synthesized

<400> SEQUENCE: 14

Ser Met Thr Leu Thr Val Gln Ala Arg Gln Leu Leu Ser Gly Ile Val
1               5                   10                  15

Gln Gln Gln Asn Asn Leu Leu Arg Ala Ile Glu Ala Gln Gln His Leu
                20                  25                  30

Leu Gln Leu Thr
        35

<210> SEQ ID NO 15
<211> LENGTH: 35
<212> TYPE: PRT
<213> ORGANISM: Artificial
<220> FEATURE:
<223> OTHER INFORMATION: synthesized

<400> SEQUENCE: 15

Met Thr Leu Thr Val Gln Ala Arg Gln Leu Leu Ser Gly Ile Val Gln
1               5                   10                  15

Gln Gln Asn Asn Leu Leu Arg Ala Ile Glu Ala Gln Gln His Leu Leu
                20                  25                  30

Gln Leu Thr
        35

<210> SEQ ID NO 16
<211> LENGTH: 36
<212> TYPE: PRT
<213> ORGANISM: Artificial
<220> FEATURE:
<223> OTHER INFORMATION: synthesized

<400> SEQUENCE: 16
```

Met Thr Leu Thr Val Gln Ala Arg Gln Leu Leu Ser Gly Ile Val Gln
1               5                   10                  15

Gln Gln Asn Asn Leu Leu Arg Ala Ile Glu Ala Gln Gln His Leu Leu
            20                  25                  30

Gln Leu Thr Val
        35

<210> SEQ ID NO 17
<211> LENGTH: 34
<212> TYPE: PRT
<213> ORGANISM: Artificial
<220> FEATURE:
<223> OTHER INFORMATION: synthesized

<400> SEQUENCE: 17

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr

<210> SEQ ID NO 18
<211> LENGTH: 35
<212> TYPE: PRT
<213> ORGANISM: Artificial
<220> FEATURE:
<223> OTHER INFORMATION: synthesized

<400> SEQUENCE: 18

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val
        35

<210> SEQ ID NO 19
<211> LENGTH: 36
<212> TYPE: PRT
<213> ORGANISM: Artificial
<220> FEATURE:
<223> OTHER INFORMATION: synthesized

<400> SEQUENCE: 19

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp
        35

<210> SEQ ID NO 20
<211> LENGTH: 37
<212> TYPE: PRT
<213> ORGANISM: Artificial
<220> FEATURE:
<223> OTHER INFORMATION: synthesized

<400> SEQUENCE: 20

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln

```
                    20                  25                  30

Leu Thr Val Trp Gly
        35

<210> SEQ ID NO 21
<211> LENGTH: 38
<212> TYPE: PRT
<213> ORGANISM: Artificial
<220> FEATURE:
<223> OTHER INFORMATION: synthesized

<400> SEQUENCE: 21

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp Gly Ile
        35

<210> SEQ ID NO 22
<211> LENGTH: 44
<212> TYPE: PRT
<213> ORGANISM: Artificial
<220> FEATURE:
<223> OTHER INFORMATION: synthesized

<400> SEQUENCE: 22

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp Gly Ile Lys Gln Leu Gln Ala Arg
        35                  40

<210> SEQ ID NO 23
<211> LENGTH: 36
<212> TYPE: PRT
<213> ORGANISM: Artificial
<220> FEATURE:
<223> OTHER INFORMATION: synthesized

<400> SEQUENCE: 23

Leu Thr Val Gln Ala Arg Gln Leu Leu Ser Gly Ile Val Gln Gln Gln
1               5                   10                  15

Asn Asn Leu Leu Arg Ala Ile Glu Ala Gln Gln His Leu Leu Gln Leu
            20                  25                  30

Thr Val Trp Gly
        35

<210> SEQ ID NO 24
<211> LENGTH: 42
<212> TYPE: PRT
<213> ORGANISM: Artificial
<220> FEATURE:
<223> OTHER INFORMATION: synthesized

<400> SEQUENCE: 24

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu
```

<210> SEQ ID NO 25
<211> LENGTH: 47
<212> TYPE: PRT
<213> ORGANISM: Artificial
<220> FEATURE:
<223> OTHER INFORMATION: synthesized

<400> SEQUENCE: 25

```
Gln Ala Arg Gln Leu Leu Ser Gly Ile Val Gln Gln Gln Asn Asn Leu
1               5                   10                  15
Leu Arg Ala Ile Glu Ala Gln Gln His Leu Leu Gln Leu Thr Val Trp
            20                  25                  30
Gly Ile Lys Gln Leu Gln Ala Arg Ile Leu Ala Val Glu Arg Tyr
        35                  40                  45
```

<210> SEQ ID NO 26
<211> LENGTH: 49
<212> TYPE: PRT
<213> ORGANISM: Artificial
<220> FEATURE:
<223> OTHER INFORMATION: synthesized

<400> SEQUENCE: 26

```
Gln Ala Arg Gln Leu Leu Ser Gly Ile Val Gln Gln Gln Asn Asn Leu
1               5                   10                  15
Leu Arg Ala Ile Glu Ala Gln Gln His Leu Leu Gln Leu Thr Val Trp
            20                  25                  30
Gly Ile Lys Gln Leu Gln Ala Arg Ile Leu Ala Val Glu Arg Tyr Leu
        35                  40                  45
Lys
```

<210> SEQ ID NO 27
<211> LENGTH: 51
<212> TYPE: PRT
<213> ORGANISM: Artificial
<220> FEATURE:
<223> OTHER INFORMATION: synthesized

<400> SEQUENCE: 27

```
Gln Ala Arg Gln Leu Leu Ser Gly Ile Val Gln Gln Gln Asn Asn Leu
1               5                   10                  15
Leu Arg Ala Ile Glu Ala Gln Gln His Leu Leu Gln Leu Thr Val Trp
            20                  25                  30
Gly Ile Lys Gln Leu Gln Ala Arg Ile Leu Ala Val Glu Arg Tyr Leu
        35                  40                  45
Lys Asp Gln
    50
```

<210> SEQ ID NO 28
<211> LENGTH: 36
<212> TYPE: PRT
<213> ORGANISM: Artificial
<220> FEATURE:
<223> OTHER INFORMATION: synthesized

<400> SEQUENCE: 28

```
Ser Gly Ile Val Gln Gln Gln Asn Asn Leu Leu Arg Ala Ile Glu Ala
1               5                   10                  15
Gln Gln His Leu Leu Gln Leu Thr Val Trp Gly Ile Lys Gln Leu Gln
            20                  25                  30
```

```
Ala Arg Ile Leu
        35

<210> SEQ ID NO 29
<211> LENGTH: 45
<212> TYPE: PRT
<213> ORGANISM: Artificial
<220> FEATURE:
<223> OTHER INFORMATION: synthesized

<400> SEQUENCE: 29

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu Ala Val Glu Arg Tyr Leu Lys Asp Gln
        35                  40                  45

<210> SEQ ID NO 30
<211> LENGTH: 41
<212> TYPE: PRT
<213> ORGANISM: Artificial
<220> FEATURE:
<223> OTHER INFORMATION: synthesized

<400> SEQUENCE: 30

Gln Gln Gln Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu
            20                  25                  30

Ala Val Glu Arg Tyr Leu Lys Asp Gln
        35                  40

<210> SEQ ID NO 31
<211> LENGTH: 34
<212> TYPE: PRT
<213> ORGANISM: Artificial
<220> FEATURE:
<223> OTHER INFORMATION: synthesized

<400> SEQUENCE: 31

Arg Ala Ile Glu Ala Gln Gln His Leu Leu Gln Leu Thr Val Trp Gly
1               5                   10                  15

Ile Lys Gln Leu Gln Ala Arg Ile Leu Ala Val Glu Arg Tyr Leu Lys
            20                  25                  30

Asp Gln

<210> SEQ ID NO 32
<211> LENGTH: 36
<212> TYPE: PRT
<213> ORGANISM: Artificial
<220> FEATURE:
<223> OTHER INFORMATION: synthesized

<400> SEQUENCE: 32

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu
        35
```

<210> SEQ ID NO 33
<211> LENGTH: 41
<212> TYPE: PRT
<213> ORGANISM: Artificial
<220> FEATURE:
<223> OTHER INFORMATION: synthesized

<400> SEQUENCE: 33

Cys Gly Gly Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu
            20                  25                  30

Ala Val Glu Arg Tyr Leu Lys Asp Gln
            35                  40

<210> SEQ ID NO 34
<211> LENGTH: 31
<212> TYPE: PRT
<213> ORGANISM: Artificial
<220> FEATURE:
<223> OTHER INFORMATION: synthesized

<400> SEQUENCE: 34

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val
            20                  25                  30

<210> SEQ ID NO 35
<211> LENGTH: 41
<212> TYPE: PRT
<213> ORGANISM: Artificial
<220> FEATURE:
<223> OTHER INFORMATION: synthesized

<400> SEQUENCE: 35

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln Gly Gly Cys
            35                  40

<210> SEQ ID NO 36
<211> LENGTH: 44
<212> TYPE: PRT
<213> ORGANISM: Artificial
<220> FEATURE:
<223> OTHER INFORMATION: synthesized

<400> SEQUENCE: 36

Cys Gly Gly Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu
            20                  25                  30

Ala Val Glu Arg Tyr Leu Lys Asp Gln Gly Gly Cys
            35                  40

<210> SEQ ID NO 37
<211> LENGTH: 39
<212> TYPE: PRT
<213> ORGANISM: Artificial
<220> FEATURE:

<223> OTHER INFORMATION: synthesized

<400> SEQUENCE: 37

Leu Ser Gly Ile Val Gln Gln Asn Asn Leu Leu Arg Ala Ile Glu
1               5                   10                  15

Ala Gln Gln His Leu Leu Gln Leu Thr Val Trp Gly Ile Lys Gln Leu
            20                  25                  30

Gln Ala Arg Ile Leu Ala Val
            35

<210> SEQ ID NO 38
<211> LENGTH: 36
<212> TYPE: PRT
<213> ORGANISM: Artificial
<220> FEATURE:
<223> OTHER INFORMATION: synthesized

<400> SEQUENCE: 38

Tyr Thr Asn Thr Ile Tyr Thr Leu Leu Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 39
<211> LENGTH: 36
<212> TYPE: PRT
<213> ORGANISM: Artificial
<220> FEATURE:
<223> OTHER INFORMATION: synthesized

<400> SEQUENCE: 39

Tyr Thr Gly Ile Ile Tyr Asn Leu Leu Glu Glu Ser Gln Asn Gln Gln
1               5                   10                  15

Glu Lys Asn Glu Gln Glu Leu Leu Glu Leu Asp Lys Trp Ala Asn Leu
            20                  25                  30

Trp Asn Trp Phe
        35

<210> SEQ ID NO 40
<211> LENGTH: 36
<212> TYPE: PRT
<213> ORGANISM: Artificial
<220> FEATURE:
<223> OTHER INFORMATION: synthesized

<400> SEQUENCE: 40

Tyr Thr Ser Leu Ile Tyr Ser Leu Leu Glu Lys Ser Gln Ile Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 41
<211> LENGTH: 36
<212> TYPE: PRT
<213> ORGANISM: Artificial
<220> FEATURE:
<223> OTHER INFORMATION: synthesized

<400> SEQUENCE: 41

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Phe Asn Phe Phe
        35

<210> SEQ ID NO 42
<211> LENGTH: 36
<212> TYPE: PRT
<213> ORGANISM: Artificial
<220> FEATURE:
<223> OTHER INFORMATION: synthesized

<400> SEQUENCE: 42

Trp Gln Glu Trp Glu Gln Lys Val Arg Tyr Leu Glu Ala Asn Ile Thr
1               5                   10                  15

Ala Leu Leu Glu Gln Ala Gln Ile Gln Gln Glu Lys Asn Glu Tyr Glu
            20                  25                  30

Leu Gln Lys Leu
        35

<210> SEQ ID NO 43
<211> LENGTH: 42
<212> TYPE: PRT
<213> ORGANISM: Artificial
<220> FEATURE:
<223> OTHER INFORMATION: synthesized

<400> SEQUENCE: 43

Asp Arg Glu Ile Asn Asn Tyr Thr Ser Leu Ile His Ser Leu Ile Glu
1               5                   10                  15

Glu Ser Gln Asn Gln Gln Glu Lys Asn Glu Gln Glu Leu Leu Glu Leu
            20                  25                  30

Asp Lys Trp Ala Ser Leu Trp Asn Trp Phe
        35                  40

<210> SEQ ID NO 44
<211> LENGTH: 48
<212> TYPE: PRT
<213> ORGANISM: Artificial
<220> FEATURE:
<223> OTHER INFORMATION: synthesized

<400> SEQUENCE: 44

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Trp Ala Ser Leu Trp Asn Trp Phe
        35                  40                  45

<210> SEQ ID NO 45
<211> LENGTH: 42
<212> TYPE: PRT
<213> ORGANISM: Artificial
<220> FEATURE:
<223> OTHER INFORMATION: synthesized

<400> SEQUENCE: 45

Asn Asn Met Thr Trp Met Glu Trp Asp Arg Glu Ile Asn Asn Tyr Thr
1               5                   10                  15

Ser Leu Ile His Ser Leu Ile Glu Glu Ser Gln Asn Gln Gln Glu Lys
            20                  25                  30

Asn Glu Gln Glu Leu Leu Glu Leu Asp Lys
        35                  40

<210> SEQ ID NO 46
<211> LENGTH: 46
<212> TYPE: PRT
<213> ORGANISM: Artificial
<220> FEATURE:
<223> OTHER INFORMATION: synthesized

<400> SEQUENCE: 46

Trp Gln Glu Trp Glu Gln Lys Val Arg Tyr Leu Glu Ala Asn Ile Thr
1               5                   10                  15

Ala Leu Leu Glu Gln Ala Gln Ile Gln Gln Glu Lys Asn Glu Tyr Glu
            20                  25                  30

Leu Gln Lys Leu Asp Lys Trp Ala Ser Leu Trp Asn Trp Phe
        35                  40                  45

<210> SEQ ID NO 47
<211> LENGTH: 50
<212> TYPE: PRT
<213> ORGANISM: Artificial
<220> FEATURE:
<223> OTHER INFORMATION: synthesized

<400> SEQUENCE: 47

Asn Asn Met Thr Trp Gln Glu Trp Glu Gln Lys Val Arg Tyr Leu Glu
1               5                   10                  15

Ala Asn Ile Thr Ala Leu Leu Glu Gln Ala Gln Ile Gln Gln Glu Lys
            20                  25                  30

Asn Glu Tyr Glu Leu Gln Lys Leu Asp Lys Trp Ala Ser Leu Trp Asn
        35                  40                  45

Trp Phe
    50

<210> SEQ ID NO 48
<211> LENGTH: 36
<212> TYPE: PRT
<213> ORGANISM: Artificial
<220> FEATURE:
<223> OTHER INFORMATION: synthesized

<400> SEQUENCE: 48

Trp Asn Trp Phe Ile Thr Ala Leu Leu Glu Gln Ala Gln Ile Gln Gln
1               5                   10                  15

Glu Lys Asn Glu Tyr Glu Leu Gln Lys Leu Asp Lys Trp Ala Ser Leu
            20                  25                  30

Trp Asn Trp Phe
        35

<210> SEQ ID NO 49
<211> LENGTH: 46
<212> TYPE: PRT
<213> ORGANISM: Artificial
<220> FEATURE:
<223> OTHER INFORMATION: synthesized

<400> SEQUENCE: 49

Trp Gln Glu Trp Asp Arg Glu Ile Ser Asn Tyr Thr Ser Leu Ile Thr
1               5                   10                  15

Ala Leu Leu Glu Gln Ala Gln Ile Gln Gln Glu Lys Asn Glu Tyr Glu
            20                  25                  30

Leu Gln Lys Leu Asp Glu Trp Ala Ser Leu Trp Glu Trp Phe
        35                  40                  45

<210> SEQ ID NO 50
<211> LENGTH: 40
<212> TYPE: PRT
<213> ORGANISM: Artificial
<220> FEATURE:
<223> OTHER INFORMATION: synthesized

<400> SEQUENCE: 50

Trp Gln Glu Trp Glu Arg Glu Ile Ser Ala Tyr Thr Ser Leu Ile Thr
1               5                   10                  15

Ala Leu Leu Glu Gln Ala Gln Ile Gln Gln Glu Lys Ile Glu Tyr Glu
            20                  25                  30

Leu Gln Lys Leu Glu Trp Glu Trp
        35                  40

<210> SEQ ID NO 51
<211> LENGTH: 39
<212> TYPE: PRT
<213> ORGANISM: Artificial
<220> FEATURE:
<223> OTHER INFORMATION: synthesized

<400> SEQUENCE: 51

Trp Gln Glu Trp Asp Arg Glu Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Asn Trp Phe
        35

<210> SEQ ID NO 52
<211> LENGTH: 39
<212> TYPE: PRT
<213> ORGANISM: Artificial
<220> FEATURE:
<223> OTHER INFORMATION: synthesized

<400> SEQUENCE: 52

Trp Gln Glu Trp Asp Arg Glu Ile Thr Ala Leu Leu Glu Gln Ala Gln
1               5                   10                  15

Ile Gln Gln Glu Lys Asn Glu Tyr Glu Leu Gln Lys Leu Asp Glu Trp
            20                  25                  30

Ala Ser Leu Trp Glu Trp Phe
        35

<210> SEQ ID NO 53
<211> LENGTH: 35
<212> TYPE: PRT
<213> ORGANISM: Artificial
<220> FEATURE:
<223> OTHER INFORMATION: synthesized

<400> SEQUENCE: 53

Trp Gln Glu Trp Asp Arg Glu Ile Thr Ala Leu Leu Glu Gln Ala Gln
1               5                   10                  15

Ile Gln Gln Glu Lys Asn Glu Tyr Glu Leu Gln Lys Leu Asp Glu Trp
            20                  25                  30

Glu Trp Phe
        35

<210> SEQ ID NO 54
<211> LENGTH: 35
<212> TYPE: PRT
<213> ORGANISM: Artificial
<220> FEATURE:
<223> OTHER INFORMATION: synthesized

<400> SEQUENCE: 54

Trp Gln Glu Trp Glu Arg Glu Ile Thr Ala Leu Leu Glu Gln Ala Gln
1               5                   10                  15

Ile Gln Gln Glu Lys Ile Glu Tyr Glu Leu Gln Lys Leu Ile Glu Trp
            20                  25                  30

Glu Trp Phe
        35

<210> SEQ ID NO 55
<211> LENGTH: 35
<212> TYPE: PRT
<213> ORGANISM: Artificial
<220> FEATURE:
<223> OTHER INFORMATION: synthesized

<400> SEQUENCE: 55

Trp Gln Glu Trp Glu Arg Glu Ile Thr Ala Leu Leu Glu Gln Ala Gln
1               5                   10                  15

Ile Gln Gln Glu Lys Asn Glu Tyr Glu Leu Gln Lys Leu Ile Glu Trp
            20                  25                  30

Glu Trp Phe
        35

<210> SEQ ID NO 56
<211> LENGTH: 35
<212> TYPE: PRT
<213> ORGANISM: Artificial
<220> FEATURE:
<223> OTHER INFORMATION: synthesized

<400> SEQUENCE: 56

Trp Gln Glu Trp Glu Arg Glu Ile Thr Ala Leu Leu Glu Gln Ala Gln
1               5                   10                  15

Ile Gln Gln Glu Lys Ile Glu Tyr Glu Leu Gln Lys Leu Asp Glu Trp
            20                  25                  30

Glu Trp Phe
        35

<210> SEQ ID NO 57
<211> LENGTH: 39
<212> TYPE: PRT
<213> ORGANISM: Artificial
<220> FEATURE:
<223> OTHER INFORMATION: synthesized

<400> SEQUENCE: 57

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Asn Trp Phe
        35

```
<210> SEQ ID NO 58
<211> LENGTH: 39
<212> TYPE: PRT
<213> ORGANISM: Artificial
<220> FEATURE:
<223> OTHER INFORMATION: synthesized

<400> SEQUENCE: 58

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Gly Leu Trp Glu Trp Phe
        35

<210> SEQ ID NO 59
<211> LENGTH: 39
<212> TYPE: PRT
<213> ORGANISM: Artificial
<220> FEATURE:
<223> OTHER INFORMATION: synthesized

<400> SEQUENCE: 59

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Ala Glu Trp
            20                  25                  30

Ala Gly Leu Trp Ala Trp Phe
        35

<210> SEQ ID NO 60
<211> LENGTH: 35
<212> TYPE: PRT
<213> ORGANISM: Artificial
<220> FEATURE:
<223> OTHER INFORMATION: synthesized

<400> SEQUENCE: 60

Trp Gln Glu Trp Glu Gln Lys Ile Thr Ala Leu Leu Glu Gln Ala Gln
1               5                   10                  15

Ile Gln Gln Glu Lys Ile Glu Tyr Glu Leu Gln Lys Leu Ile Glu Trp
            20                  25                  30

Glu Trp Phe
        35

<210> SEQ ID NO 61
<211> LENGTH: 41
<212> TYPE: PRT
<213> ORGANISM: Artificial
<220> FEATURE:
<223> OTHER INFORMATION: synthesized

<400> SEQUENCE: 61

Gln Gln Gln Asn Asn Leu Leu Arg Ala Ile Glu Ala Gln Gln His Leu
1               5                   10                  15

Leu Gln Leu Thr Ala Trp Gly Ile Lys Gln Leu Gln Ala Arg Ile Leu
            20                  25                  30

Ala Val Glu Arg Tyr Leu Lys Asp Gln
        35                  40

<210> SEQ ID NO 62
```

<211> LENGTH: 41
<212> TYPE: PRT
<213> ORGANISM: Artificial
<220> FEATURE:
<223> OTHER INFORMATION: synthesized

<400> SEQUENCE: 62

```
Gln Gln Gln Asn Asn Leu Leu Arg Ala Ile Glu Ala Gln Gln His Leu
1               5                   10                  15
Leu Gln Leu Thr Val Ala Gly Ile Lys Gln Leu Gln Ala Arg Ile Leu
            20                  25                  30
Ala Val Glu Arg Tyr Leu Lys Asp Gln
        35                  40
```

<210> SEQ ID NO 63
<211> LENGTH: 49
<212> TYPE: PRT
<213> ORGANISM: Artificial
<220> FEATURE:
<223> OTHER INFORMATION: synthesized

<400> SEQUENCE: 63

```
Gln Ala Arg Gln Leu Leu Ser Gly Ile Val Gln Gln Asn Asn Leu
1               5                   10                  15
Leu Arg Ala Ile Glu Ala Gln Gln His Ala Leu Gln Ala Thr Val Trp
            20                  25                  30
Gly Ile Lys Gln Leu Gln Ala Arg Ile Leu Ala Val Glu Arg Tyr Leu
        35                  40                  45
Lys
```

<210> SEQ ID NO 64
<211> LENGTH: 51
<212> TYPE: PRT
<213> ORGANISM: Artificial
<220> FEATURE:
<223> OTHER INFORMATION: synthesized

<400> SEQUENCE: 64

```
Gln Ala Arg Gln Leu Leu Ser Gly Ile Val Gln Gln Asn Asn Leu
1               5                   10                  15
Leu Arg Ala Ile Glu Ala Gln Gln His Ala Leu Gln Ala Thr Val Trp
            20                  25                  30
Gly Ile Lys Gln Leu Gln Ala Arg Ile Leu Ala Val Glu Arg Tyr Leu
        35                  40                  45
Lys Asp Gln
    50
```

<210> SEQ ID NO 65
<211> LENGTH: 49
<212> TYPE: PRT
<213> ORGANISM: Artificial
<220> FEATURE:
<223> OTHER INFORMATION: synthesized

<400> SEQUENCE: 65

```
Gln Ala Arg Gln Leu Val Ser Gly Leu Val Gln Gln Asn Asn Ile
1               5                   10                  15
Leu Arg Ala Leu Glu Ala Thr Gln His Ala Val Gln Ala Leu Val Trp
            20                  25                  30
Gly Val Lys Gln Leu Gln Ala Arg Val Leu Ala Leu Glu Arg Tyr Ile
        35                  40                  45
```

Lys

<210> SEQ ID NO 66
<211> LENGTH: 49
<212> TYPE: PRT
<213> ORGANISM: Artificial
<220> FEATURE:
<223> OTHER INFORMATION: synthesized

<400> SEQUENCE: 66

Gln Ile Arg Gln Leu Leu Ser Gly Ile Val Gln Gln Gln Asn Asn Leu
1               5                   10                  15

Leu Arg Ala Ile Glu Ala Ile Gln His Ala Leu Gln Ala Ile Val Trp
            20                  25                  30

Gly Ile Lys Gln Leu Gln Ala Arg Ile Leu Ala Val Glu Arg Tyr Leu
        35                  40                  45

Lys

<210> SEQ ID NO 67
<211> LENGTH: 49
<212> TYPE: PRT
<213> ORGANISM: Artificial
<220> FEATURE:
<223> OTHER INFORMATION: synthesized

<400> SEQUENCE: 67

Gln Ala Arg Gln Leu Val Ser Gly Leu Val Gln Gln Gln Asn Asn Ile
1               5                   10                  15

Leu Arg Ala Leu Glu Ala Thr Gln His Ala Val Gln Ala Leu Val Trp
            20                  25                  30

Gly Val Arg Gln Leu Gln Ala Arg Val Leu Ala Leu Glu Arg Tyr Ile
        35                  40                  45

Lys

<210> SEQ ID NO 68
<211> LENGTH: 51
<212> TYPE: PRT
<213> ORGANISM: Artificial
<220> FEATURE:
<223> OTHER INFORMATION: synthesized

<400> SEQUENCE: 68

Gln Ala Arg Gln Leu Leu Ser Gly Ile Val Gln Gln Gln Asn Asn Leu
1               5                   10                  15

Leu Arg Ala Ile Glu Ala Thr Gln His Ala Val Gln Ala Leu Val Trp
            20                  25                  30

Gly Val Lys Gln Leu Gln Ala Arg Val Leu Ala Leu Glu Arg Tyr Ile
        35                  40                  45

Lys Asp Gln
    50

<210> SEQ ID NO 69
<211> LENGTH: 51
<212> TYPE: PRT
<213> ORGANISM: Artificial
<220> FEATURE:
<223> OTHER INFORMATION: synthesized

<400> SEQUENCE: 69

Gln Ala Arg Gln Leu Val Ser Gly Leu Val Gln Gln Gln Asn Asn Ile
1               5                   10                  15

```
Leu Arg Ala Leu Glu Ala Gln Gln His Ala Leu Gln Ala Thr Val Trp
            20                  25                  30

Gly Ile Lys Gln Leu Gln Ala Arg Val Leu Ala Leu Glu Arg Tyr Ile
        35                  40                  45

Lys Asp Gln
    50

<210> SEQ ID NO 70
<211> LENGTH: 51
<212> TYPE: PRT
<213> ORGANISM: Artificial
<220> FEATURE:
<223> OTHER INFORMATION: synthesized

<400> SEQUENCE: 70

Gln Ala Arg Gln Leu Leu Ser Gly Ile Val Gln Gln Asn Asn Leu
1               5                   10                  15

Leu Arg Ala Ile Glu Ala Gln Gln His Ala Leu Gln Ala Thr Val Trp
            20                  25                  30

Gly Val Lys Gln Leu Gln Ala Arg Ile Leu Ala Val Glu Arg Tyr Leu
        35                  40                  45

Lys Asp Gln
    50

<210> SEQ ID NO 71
<211> LENGTH: 41
<212> TYPE: PRT
<213> ORGANISM: Artificial
<220> FEATURE:
<223> OTHER INFORMATION: synthesized

<400> SEQUENCE: 71

Gln Gln Gln Asn Asn Leu Leu Arg Ala Ile Glu Ala Gln Gln His Leu
1               5                   10                  15

Leu Gln Leu Thr Val Phe Gly Ile Lys Gln Leu Gln Ala Arg Ile Leu
            20                  25                  30

Ala Val Glu Arg Tyr Leu Lys Asp Gln
        35                  40

<210> SEQ ID NO 72
<211> LENGTH: 49
<212> TYPE: PRT
<213> ORGANISM: Artificial
<220> FEATURE:
<223> OTHER INFORMATION: synthesized

<400> SEQUENCE: 72

Gln Ala Arg Gln Leu Leu Ser Gly Ile Val Gln Gln Asn Asn Leu
1               5                   10                  15

Leu Arg Ala Ile Glu Ala Gln Gln His Leu Leu Gln Leu Thr Val Phe
            20                  25                  30

Gly Ile Arg Gln Leu Gln Ala Arg Ile Leu Ala Val Glu Arg Tyr Leu
        35                  40                  45

Lys

<210> SEQ ID NO 73
<211> LENGTH: 51
<212> TYPE: PRT
<213> ORGANISM: Artificial
<220> FEATURE:
<223> OTHER INFORMATION: synthesized
```

```
<400> SEQUENCE: 73

Gln Ala Arg Gln Leu Leu Ser Gly Ile Val Gln Gln Asn Asn Leu
1               5                   10                  15

Leu Arg Ala Ile Glu Ala Gln Gln His Leu Leu Gln Ala Thr Val Trp
            20                  25                  30

Gly Ile Lys Gln Leu Gln Ala Arg Ile Leu Ala Val Glu Arg Tyr Leu
        35                  40                  45

Lys Asp Gln
        50

<210> SEQ ID NO 74
<211> LENGTH: 41
<212> TYPE: PRT
<213> ORGANISM: Artificial
<220> FEATURE:
<223> OTHER INFORMATION: synthesized

<400> SEQUENCE: 74

Gln Gln Gln Asn Asn Leu Leu Arg Ala Ile Glu Ala Gln Gln His Leu
1               5                   10                  15

Leu Gln Ala Thr Val Trp Gly Ile Lys Gln Leu Gln Ala Arg Ile Leu
            20                  25                  30

Ala Val Glu Arg Tyr Leu Lys Asp Gln
        35                  40

<210> SEQ ID NO 75
<211> LENGTH: 36
<212> TYPE: PRT
<213> ORGANISM: Artificial
<220> FEATURE:
<223> OTHER INFORMATION: synthesized

<400> SEQUENCE: 75

Asn Ala Ser Trp Ser Asn Lys Ser Leu Glu Gln Ile Trp Asn Asn Met
1               5                   10                  15

Thr Trp Met Glu Trp Asp Arg Glu Ile Asn Asn Tyr Thr Ser Leu Ile
            20                  25                  30

His Ser Leu Ile
        35

<210> SEQ ID NO 76
<211> LENGTH: 36
<212> TYPE: PRT
<213> ORGANISM: Artificial
<220> FEATURE:
<223> OTHER INFORMATION: synthesized

<400> SEQUENCE: 76

Asn Lys Ser Leu Glu Gln Ile Trp Asn Asn Met Thr Trp Met Glu Trp
1               5                   10                  15

Asp Arg Glu Ile Asn Asn Tyr Thr Ser Leu Ile His Ser Leu Ile Glu
            20                  25                  30

Glu Ser Gln Asn
        35

<210> SEQ ID NO 77
<211> LENGTH: 36
<212> TYPE: PRT
<213> ORGANISM: Artificial
<220> FEATURE:
<223> OTHER INFORMATION: synthesized
```

-continued

<400> SEQUENCE: 77

Lys Ser Leu Glu Gln Ile Trp Asn Asn Met Thr Trp Met Glu Trp Asp
1               5                   10                  15

Arg Glu Ile Asn Asn Tyr Thr Ser Leu Ile His Ser Leu Ile Glu Glu
            20                  25                  30

Ser Gln Asn Gln
        35

<210> SEQ ID NO 78
<211> LENGTH: 36
<212> TYPE: PRT
<213> ORGANISM: Artificial
<220> FEATURE:
<223> OTHER INFORMATION: synthesized

<400> SEQUENCE: 78

Ser Leu Glu Gln Ile Trp Asn Asn Met Thr Trp Met Glu Trp Asp Arg
1               5                   10                  15

Glu Ile Asn Asn Tyr Thr Ser Leu Ile His Ser Leu Ile Glu Glu Ser
            20                  25                  30

Gln Asn Gln Gln
        35

<210> SEQ ID NO 79
<211> LENGTH: 36
<212> TYPE: PRT
<213> ORGANISM: Artificial
<220> FEATURE:
<223> OTHER INFORMATION: synthesized

<400> SEQUENCE: 79

Leu Glu Gln Ile Trp Asn Asn Met Thr Trp Met Glu Trp Asp Arg Glu
1               5                   10                  15

Ile Asn Asn Tyr Thr Ser Leu Ile His Ser Leu Ile Glu Glu Ser Gln
            20                  25                  30

Asn Gln Gln Glu
        35

<210> SEQ ID NO 80
<211> LENGTH: 36
<212> TYPE: PRT
<213> ORGANISM: Artificial
<220> FEATURE:
<223> OTHER INFORMATION: synthesized

<400> SEQUENCE: 80

Glu Gln Ile Trp Asn Asn Met Thr Trp Met Glu Trp Asp Arg Glu Ile
1               5                   10                  15

Asn Asn Tyr Thr Ser Leu Ile His Ser Leu Ile Glu Glu Ser Gln Asn
            20                  25                  30

Gln Gln Glu Lys
        35

<210> SEQ ID NO 81
<211> LENGTH: 36
<212> TYPE: PRT
<213> ORGANISM: Artificial
<220> FEATURE:
<223> OTHER INFORMATION: synthesized

<400> SEQUENCE: 81

Gln Ile Trp Asn Asn Met Thr Trp Met Glu Trp Asp Arg Glu Ile Asn

```
                1               5                  10                 15
Asn Tyr Thr Ser Leu Ile His Ser Leu Ile Glu Glu Ser Gln Asn Gln
                20                 25                 30

Gln Glu Lys Asn
            35

<210> SEQ ID NO 82
<211> LENGTH: 36
<212> TYPE: PRT
<213> ORGANISM: Artificial
<220> FEATURE:
<223> OTHER INFORMATION: synthesized

<400> SEQUENCE: 82

Ile Trp Asn Asn Met Thr Trp Met Glu Trp Asp Arg Glu Ile Asn Asn
1               5                   10                  15

Tyr Thr Ser Leu Ile His Ser Leu Ile Glu Glu Ser Gln Asn Gln Gln
                20                  25                  30

Glu Lys Asn Glu
            35

<210> SEQ ID NO 83
<211> LENGTH: 36
<212> TYPE: PRT
<213> ORGANISM: Artificial
<220> FEATURE:
<223> OTHER INFORMATION: synthesized

<400> SEQUENCE: 83

Trp Asn Asn Met Thr Trp Met Glu Trp Asp Arg Glu Ile Asn Asn Tyr
1               5                   10                  15

Thr Ser Leu Ile His Ser Leu Ile Glu Glu Ser Gln Asn Gln Gln Glu
                20                  25                  30

Lys Asn Glu Gln
            35

<210> SEQ ID NO 84
<211> LENGTH: 36
<212> TYPE: PRT
<213> ORGANISM: Artificial
<220> FEATURE:
<223> OTHER INFORMATION: synthesized

<400> SEQUENCE: 84

Asn Asn Met Thr Trp Met Glu Trp Asp Arg Glu Ile Asn Asn Tyr Thr
1               5                   10                  15

Ser Leu Ile His Ser Leu Ile Glu Glu Ser Gln Asn Gln Gln Glu Lys
                20                  25                  30

Asn Glu Gln Glu
            35

<210> SEQ ID NO 85
<211> LENGTH: 36
<212> TYPE: PRT
<213> ORGANISM: Artificial
<220> FEATURE:
<223> OTHER INFORMATION: synthesized

<400> SEQUENCE: 85

Asn Met Thr Trp Met Glu Trp Asp Arg Glu Ile Asn Asn Tyr Thr Ser
1               5                   10                  15

Leu Ile His Ser Leu Ile Glu Glu Ser Gln Asn Gln Gln Glu Lys Asn
```

```
                    20                  25                  30

Glu Gln Glu Leu
        35

<210> SEQ ID NO 86
<211> LENGTH: 36
<212> TYPE: PRT
<213> ORGANISM: Artificial
<220> FEATURE:
<223> OTHER INFORMATION: synthesized

<400> SEQUENCE: 86

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu
        35

<210> SEQ ID NO 87
<211> LENGTH: 36
<212> TYPE: PRT
<213> ORGANISM: Artificial
<220> FEATURE:
<223> OTHER INFORMATION: synthesized

<400> SEQUENCE: 87

Thr Trp Met Glu Trp Asp Arg Glu Ile Asn Asn Tyr Thr Ser Leu Ile
1               5                   10                  15

His Ser Leu Ile Glu Glu Ser Gln Asn Gln Gln Glu Lys Asn Glu Gln
            20                  25                  30

Glu Leu Leu Glu
        35

<210> SEQ ID NO 88
<211> LENGTH: 36
<212> TYPE: PRT
<213> ORGANISM: Artificial
<220> FEATURE:
<223> OTHER INFORMATION: synthesized

<400> SEQUENCE: 88

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu
        35

<210> SEQ ID NO 89
<211> LENGTH: 35
<212> TYPE: PRT
<213> ORGANISM: Artificial
<220> FEATURE:
<223> OTHER INFORMATION: synthesized

<400> SEQUENCE: 89

Met Glu Trp Asp Arg Glu Ile Asn Asn Tyr Thr Ser Leu Ile His Ser
1               5                   10                  15

Leu Ile Glu Glu Ser Gln Asn Gln Gln Glu Lys Asn Glu Gln Glu Leu
            20                  25                  30

Leu Glu Asp
```

<210> SEQ ID NO 90
<211> LENGTH: 36
<212> TYPE: PRT
<213> ORGANISM: Artificial
<220> FEATURE:
<223> OTHER INFORMATION: synthesized

<400> SEQUENCE: 90

Glu Trp Asp Arg Glu Ile Asn Asn Tyr Thr Ser Leu Ile His Ser Leu
1               5                   10                  15

Ile Glu Glu Ser Gln Asn Gln Gln Glu Lys Asn Glu Gln Glu Leu Leu
            20                  25                  30

Glu Leu Asp Lys
        35

<210> SEQ ID NO 91
<211> LENGTH: 36
<212> TYPE: PRT
<213> ORGANISM: Artificial
<220> FEATURE:
<223> OTHER INFORMATION: synthesized

<400> SEQUENCE: 91

Trp Asp Arg Glu Ile Asn Asn Tyr Thr Ser Leu Ile His Ser Leu Ile
1               5                   10                  15

Glu Glu Ser Gln Asn Gln Gln Glu Lys Asn Glu Gln Glu Leu Leu Glu
            20                  25                  30

Leu Asp Lys Trp
        35

<210> SEQ ID NO 92
<211> LENGTH: 36
<212> TYPE: PRT
<213> ORGANISM: Artificial
<220> FEATURE:
<223> OTHER INFORMATION: synthesized

<400> SEQUENCE: 92

Asn Tyr Thr Ser Leu Ile His Ser Leu Ile Glu Glu Ser Gln Asn Gln
1               5                   10                  15

Gln Glu Lys Asn Glu Gln Glu Leu Leu Glu Leu Asp Lys Trp Ala Ser
            20                  25                  30

Leu Trp Asn Trp
        35

<210> SEQ ID NO 93
<211> LENGTH: 36
<212> TYPE: PRT
<213> ORGANISM: Artificial
<220> FEATURE:
<223> OTHER INFORMATION: synthesized

<400> SEQUENCE: 93

Thr Ser Leu Ile His Ser Leu Ile Glu Glu Ser Gln Asn Gln Gln Glu
1               5                   10                  15

Lys Asn Glu Gln Glu Leu Leu Glu Leu Asp Lys Trp Ala Ser Leu Trp
            20                  25                  30

Asn Trp Phe Asn
        35

```
<210> SEQ ID NO 94
<211> LENGTH: 36
<212> TYPE: PRT
<213> ORGANISM: Artificial
<220> FEATURE:
<223> OTHER INFORMATION: synthesized

<400> SEQUENCE: 94

Ser Leu Ile His Ser Leu Ile Glu Glu Ser Gln Asn Gln Gln Glu Lys
1               5                   10                  15

Asn Glu Gln Glu Leu Leu Glu Leu Asp Lys Trp Ala Ser Leu Trp Asn
                20                  25                  30

Trp Phe Asn Ile
            35

<210> SEQ ID NO 95
<211> LENGTH: 36
<212> TYPE: PRT
<213> ORGANISM: Artificial
<220> FEATURE:
<223> OTHER INFORMATION: synthesized

<400> SEQUENCE: 95

Leu Ile His Ser Leu Ile Glu Glu Ser Gln Asn Gln Gln Glu Lys Asn
1               5                   10                  15

Glu Gln Glu Leu Leu Glu Leu Asp Lys Trp Ala Ser Leu Trp Asn Trp
                20                  25                  30

Phe Asn Ile Thr
            35

<210> SEQ ID NO 96
<211> LENGTH: 43
<212> TYPE: PRT
<213> ORGANISM: Artificial
<220> FEATURE:
<223> OTHER INFORMATION: synthesized

<400> SEQUENCE: 96

Lys Ser Leu Glu Gln Ile Trp Asn Asn Met Thr Trp Met Glu Trp Glu
1               5                   10                  15

Arg Glu Ile Asp Asn Tyr Thr Ser Leu Ile Tyr Ser Leu Ile Glu Glu
                20                  25                  30

Ser Gln Asn Gln Gln Glu Lys Asn Glu Gln Glu
            35                  40

<210> SEQ ID NO 97
<211> LENGTH: 36
<212> TYPE: PRT
<213> ORGANISM: Artificial
<220> FEATURE:
<223> OTHER INFORMATION: synthesized

<400> SEQUENCE: 97

Asn Asn Met Thr Trp Met Glu Trp Glu Arg Glu Ile Asp Asn Tyr Thr
1               5                   10                  15

Ser Leu Ile Tyr Ser Leu Ile Glu Glu Ser Gln Asn Gln Gln Glu Lys
                20                  25                  30

Asn Glu Gln Glu
            35

<210> SEQ ID NO 98
<211> LENGTH: 30
<212> TYPE: PRT
```

<210> ORGANISM: Artificial
<220> FEATURE:
<223> OTHER INFORMATION: synthesized

<400> SEQUENCE: 98

Glu Trp Glu Arg Glu Ile Asp Asn Tyr Thr Ser Leu Ile Tyr Ser Leu
1               5                   10                  15

Ile Glu Glu Ser Gln Asn Gln Gln Glu Lys Asn Glu Gln Glu
            20                  25                  30

<210> SEQ ID NO 99
<211> LENGTH: 29
<212> TYPE: PRT
<213> ORGANISM: Artificial
<220> FEATURE:
<223> OTHER INFORMATION: synthesized

<400> SEQUENCE: 99

Ser Leu Glu Gln Ile Trp Asn Asn Met Thr Trp Met Glu Trp Glu Arg
1               5                   10                  15

Glu Ile Asp Asn Tyr Thr Ser Leu Ile Tyr Ser Leu Ile
            20                  25

<210> SEQ ID NO 100
<211> LENGTH: 147
<212> TYPE: DNA
<213> ORGANISM: Artificial
<220> FEATURE:
<223> OTHER INFORMATION: synthesized

<400> SEQUENCE: 100
caggctcgtc agctgctgtc tggtatcgtt cagcagcaga acaacctgct gcgtgctatc      60
gaagctcagc agcacgctct gcaggctacc gtttggggta tcaaacagct gcaggctcgt     120
atcctggctg ttgaacgtta cctgaaa                                         147

<210> SEQ ID NO 101
<211> LENGTH: 147
<212> TYPE: DNA
<213> ORGANISM: Artificial
<220> FEATURE:
<223> OTHER INFORMATION: synthesized

<400> SEQUENCE: 101
caggctcgtc agctggtttc tggtctggtt cagcagcaga acaacatcct gcgtgctctg      60
gaagctaccc agcacgctgt tcaggctctg gtttggggtg ttaaacagct gcaggctcgt     120
gttctggctc tggaacgtta catcaaa                                         147

<210> SEQ ID NO 102
<211> LENGTH: 147
<212> TYPE: DNA
<213> ORGANISM: Artificial
<220> FEATURE:
<223> OTHER INFORMATION: synthesized

<400> SEQUENCE: 102
cagatccgtc agctgctgtc tggtatcgtt cagcagcaga acaacctgct gcgtgctatc      60
gaagctatcc agcacgctct gcaggctatc gtttggggta tcaaacagct gcaggctcgt     120
atcctggctg ttgaacgtta cctgaaa                                         147

<210> SEQ ID NO 103
<211> LENGTH: 123

<212> TYPE: DNA
<213> ORGANISM: Artificial
<220> FEATURE:
<223> OTHER INFORMATION: synthesized

<400> SEQUENCE: 103
cagcagcaga acaacctgct gcgtgctatc gaagctcagc agcacctgct gcagctgacc    60
gcttggggta tcaaacagct gcaggctcgt atcctggctg ttgaacgtta cctgaaagac   120
cag                                                                 123

<210> SEQ ID NO 104
<211> LENGTH: 123
<212> TYPE: DNA
<213> ORGANISM: Artificial
<220> FEATURE:
<223> OTHER INFORMATION: synthesized

<400> SEQUENCE: 104
cagcagcaga acaacctgct gcgtgctatc gaagctcagc agcacctgct gcagctgacc    60
gttgctggta tcaaacagct gcaggctcgt atcctggctg ttgaacgtta cctgaaagac   120
cag                                                                 123

<210> SEQ ID NO 105
<211> LENGTH: 108
<212> TYPE: DNA
<213> ORGANISM: Artificial
<220> FEATURE:
<223> OTHER INFORMATION: synthesized

<400> SEQUENCE: 105
tacacctctc tgatccactc tctgatcgaa gaatctcaga accagcagga aaaaaacgaa    60
caggaactgc tggaactgga caaatgggct tctctgtgga actggttc                108

<210> SEQ ID NO 106
<211> LENGTH: 117
<212> TYPE: DNA
<213> ORGANISM: Artificial
<220> FEATURE:
<223> OTHER INFORMATION: synthesized

<400> SEQUENCE: 106
tggcaggaat gggaacagaa aatcaccgct ctgctggaac aggctcagat ccagcaggaa    60
aaaaacgaat acgaactgca gaaactggac aaatgggctt ctctgtggga atggttc      117

<210> SEQ ID NO 107
<211> LENGTH: 147
<212> TYPE: DNA
<213> ORGANISM: Artificial
<220> FEATURE:
<223> OTHER INFORMATION: synthesized

<400> SEQUENCE: 107
caggcccgcc agctgctgtc cggcatcgtg cagcagcaga caacctgct gcgcgccatc     60 gaggcccagc agcacgccct gcaggccacc gtgtgggca tcaagcagct gcaggcccgc   120
atcctggccg tggagcgcta cctgaag                                       147

<210> SEQ ID NO 108
<211> LENGTH: 147
<212> TYPE: DNA
<213> ORGANISM: Artificial

```
<220> FEATURE:
<223> OTHER INFORMATION: synthesized

<400> SEQUENCE: 108
caggcccgcc agctggtgtc cggccgcgtg cagcagcaga acaacatcct gcgcgccctg      60
gaggccaccc agcacgccgt gcaggccctg gtgtggggcg tgaagcagct gcaggcccgc     120
gtgctggccc tggagcgcta catcaag                                         147

<210> SEQ ID NO 109
<211> LENGTH: 147
<212> TYPE: DNA
<213> ORGANISM: Artificial
<220> FEATURE:
<223> OTHER INFORMATION: synthesized

<400> SEQUENCE: 109
cagatccgcc agctgctgtc cggcatcgtg cagcagcaga acaacctgct gcgcgccatc      60
gaggccatcc agcacgccct gcaggccatc gtgtggggca tcaagcagct gcaggcccgc     120
atcctggccg tggagcgcta cctgaag                                         147

<210> SEQ ID NO 110
<211> LENGTH: 123
<212> TYPE: DNA
<213> ORGANISM: Artificial
<220> FEATURE:
<223> OTHER INFORMATION: synthesized

<400> SEQUENCE: 110
cagcagcaga acaacctgct gcgcgccatc gaggcccagc agcacctgct gcagctgacc      60
gcctggggca tcaagcagct gcaggcccgc atcctggccg tggagcgcta cctgaaggac     120
cag                                                                   123

<210> SEQ ID NO 111
<211> LENGTH: 123
<212> TYPE: DNA
<213> ORGANISM: Artificial
<220> FEATURE:
<223> OTHER INFORMATION: synthesized

<400> SEQUENCE: 111
cagcagcaga acaacctgct gcgcgccatc gaggcccagc agcacctgct gcagctgacc      60
gtggccggca tcaagcagct gcaggcccgc atcctggccg tggagcgcta cctgaaggac     120
cag                                                                   123

<210> SEQ ID NO 112
<211> LENGTH: 108
<212> TYPE: DNA
<213> ORGANISM: Artificial
<220> FEATURE:
<223> OTHER INFORMATION: synthesized

<400> SEQUENCE: 112
tacacctccc tgatccactc cctgatcgag gagtcccaga accagcagga gaagaacgag      60
caggagctgc tggagctgga caagtgggcc tccctgtgga actggttc                  108

<210> SEQ ID NO 113
<211> LENGTH: 117
<212> TYPE: DNA
<213> ORGANISM: Artificial
<220> FEATURE:
```

-continued

```
<223> OTHER INFORMATION: synthesized

<400> SEQUENCE: 113
tggcaggagt gggagcagaa gatcaccgcc ctgctggagc aggcccagat ccagcaggag     60
aagaacgagt acgagctgca gaagctggac aagtgggcct ccctgtggga gtggttc       117

<210> SEQ ID NO 114
<211> LENGTH: 36
<212> TYPE: PRT
<213> ORGANISM: Artificial
<220> FEATURE:
<223> OTHER INFORMATION: synthesized

<400> SEQUENCE: 114

Leu Thr Trp Gln Glu Trp Asp Arg Glu Ile Asn Asn Tyr Thr Ser Leu
1               5                   10                  15

Ile Tyr Ser Leu Ile Glu Glu Ser Gln Asn Gln Gln Glu Glu Asn Glu
            20                  25                  30

Gln Glu Leu Leu
        35
```

ANTIVIRAL PEPTIDE-POLYMER CONJUGATE COMPRISING A POLYMER COVALENTLY ATTACHED TO TWO OR MORE SYNTHETIC HIV GP41 HR1 AND/OR HR2 PEPTIDES

This application claims the benefit of the U.S. Provisional Application 60/414,439 filed on 27 Sep. 2002.

FIELD OF THE INVENTION

The present invention relates to conjugates comprised of polymer and synthetic peptides derived from Human Immunodeficiency Virus (HIV) gp41. More particularly, the present invention comprises a conjugate formed by operably binding to a polymer no less than two molecules of synthetic peptide comprising an amino acid sequence derived from either the HR1 region or the HR2 region of HIV-1 gp41.

BACKGROUND OF THE INVENTION

It is now well known that cells can be infected by HIV through a process by which fusion occurs between the cellular membrane and the viral membrane. The generally accepted model of this process is that the viral envelope glycoprotein complex (gp120/gp41) interact with cell surface receptors on the membranes of the target cells. Following binding of gp120 to cellular receptors (e.g., CD4 in combination with a chemokine co-receptor such as CCR-5 or CXCR-4), induced is a conformational change in the gp120/gp41 complex that allows gp41 to insert into the membrane of the target cell and mediate membrane fusion.

Figure 1:
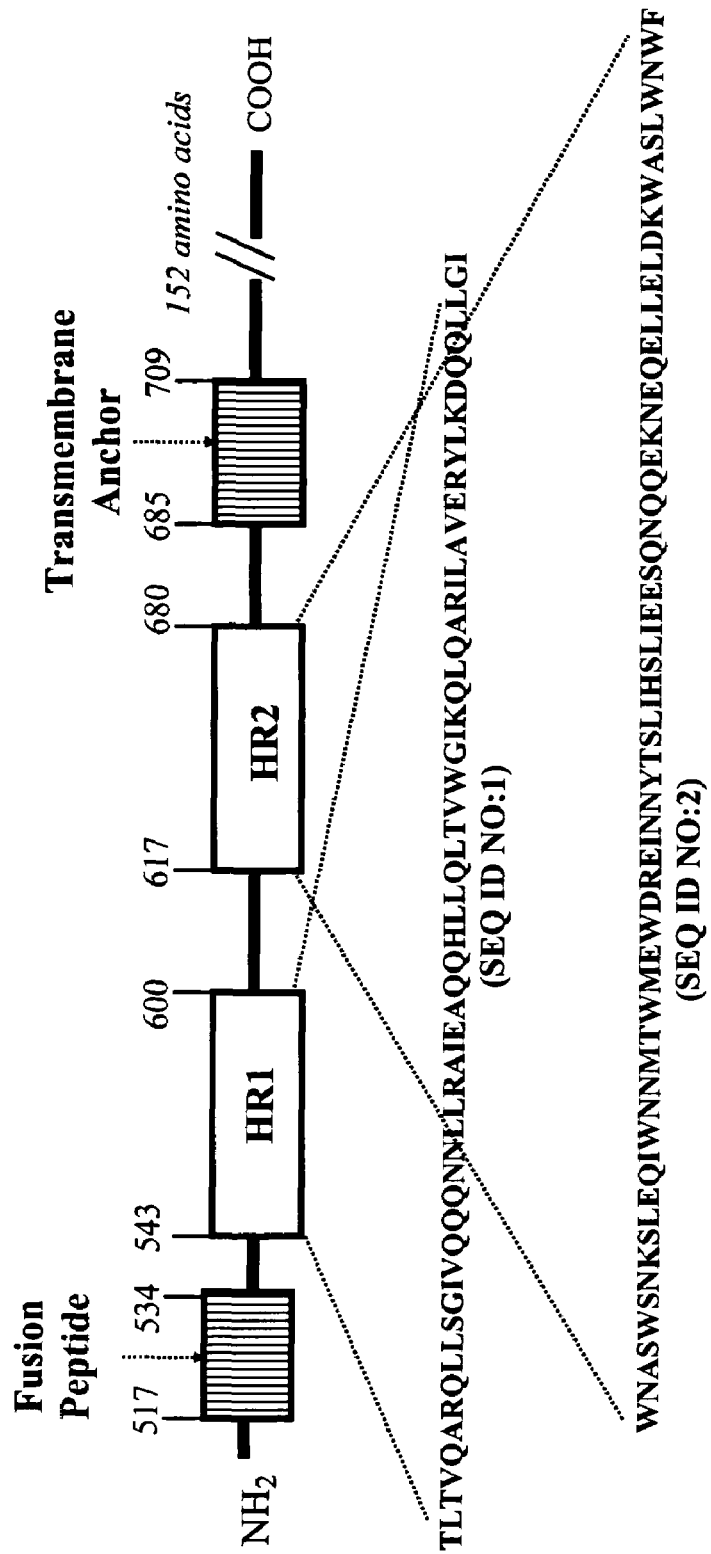

The amino acid sequence of gp41, and its variation among different strains of HIV, are well known. FIG. 1 is a schematic representation of the generally accepted functional domains of gp41 (note the amino acid sequence numbers may vary slightly depending on the HIV strain). The fusion peptide (fusogenic domain) is believed to be involved in insertion into and disruption of the target cell membrane. The transmembrane domain, containing the transmembrane anchor sequence, is located at the C-terminal end of the protein. Between the fusion peptide and transmembrane anchor are two distinct regions, known as heptad repeat (HR) regions, each region having a plurality of heptads. The HR1 region, nearer to the N-terminal end of the protein than the HR2 region, has been generally described as comprising the amino acid sequence having the sequence of SEQ ID NO:1. However, due to naturally occurring polymorphisms, the amino acid sequence (and also numbering of residues) of the HR1 region of HIV-1 gp41 may vary, depending on the viral strain from which the amino acid sequence was deduced. The other region, HR2, also depicted in FIG. 1 and SEQ ID NO:2, can also vary with polymorphisms thereof. The amino acid sequence comprising the HR1 region and the amino acid sequence comprising the HR2 region are each one of the most highly conserved regions in the HIV-1 envelope protein (Shu et al., 1999, *Biochemistry,* 38:5378-5385; Hanna et al., 2002, *AIDS* 16:1603-8). The HR regions have a plurality of 7 amino acid residue stretches or "heptads" (the 7 amino acids in each heptad designated "a" through "g"), wherein the amino acids in the "a" position and "d" position are generally hydrophobic. Also present in each HR region is one or more leucine zipper-like motifs (also referred to as "leucine zipper-like repeats") comprising an 8 amino acid sequence initiating with, and ending with, an isoleucine or leucine. Most frequently, the HR2 region has just one leucine zipper like-motif, whereas the HR1 region has five leucine zipper-like motifs. Heptads and leucine zipper-like motifs contribute to formation of a coiled coil structure of gp41 and of a coiled coil structure of peptides derived from the HR regions. Generally, coiled coils are known to be comprised of two or more helices that wrap around each other in forming oligomers, with the hallmark of coiled coils being a heptad repeat of amino acids with a predominance of hydrophobic residues at the first ("a") and fourth ("d") positions, charged residues frequently at the fifth ("e") and seventh ("g") positions, and with the amino acids in the "a" position and "d" position being determinants that influence the oligomeric state and strand orientation (see, e.g., Akey et al., 2001, *Biochemistry,* 40:6352-60).

It was discovered that synthetic peptides derived from either the HR1 region ("HR1 peptides") or HR2 region ("HR2 peptides") of HIV gp41 inhibit transmission of HIV to host cells both in in vitro assays and in in vivo clinical studies (see, e.g., Wild et al., 1994, *Proc. Natl. Acad. Sci. USA,* 91:9770-9774; U.S. Pat. Nos. 5,464,933 and 5,656,480 licensed to the present assignee; and Kilby et al., 1998, *Nature Med.* 4:1302-1306). More particularly, HR1 peptides as exemplified by DP107 (also known as T-21; SEQ ID NO:3) blocked infection of T cells with 50% effective concentration values (EC50) of 1 µg/ml (see, e.g., Lawless et al., 1996, *Biochemistry,* 35:13697-13708). HR2 peptides, as exemplified by DP178 (also known as T-20; SEQ ID NO:4) typically blocked infection of T cells with 50% effective concentration values (EC50) in the ng/ml range. Pioneering potent synthetic peptides, which comprise one or more enhancer sequences linked to a core HIV gp41 amino acid sequence, inhibit HIV membrane fusion, thereby preventing transmission of the virus to a host cell, have been described previously (see, e.g., U.S. Pat. Nos. 6,258,782 and 6,348,568 assigned to the present assignee). However, HIV gp41-derived synthetic peptides have a relatively low molecular weight. Like other peptides known in the art, in order to be effective as therapeutic agents, such synthetic peptides must be administered frequently (e.g., daily injections) to attain and maintain a level in the bloodstream sufficient for a therapeutic effect. In efforts to overcome this limitation, researchers have attempted to chemically modify a therapeutic agent, such as a peptide or peptidomimetic, by, for example, linking the therapeutic agent to a water-soluble polymer such as polyethylene glycol (PEG) so as to enable the therapeutic agent to survive longer in vivo (e.g., to increase the half-life in the bloodstream and/or to inhibit degradation of the therapeutic agent in the bloodstream). However, as known to those skilled in the art (see, e.g., U.S. Pat. Nos. 6,258,774 and 6,113,906), such modifications to the therapeutic agent have inherent limitations, i.e. such modifications typically limit the bioavailability of the therapeutic agent. More particularly, attaching a water-soluble polymer to a therapeutic agent, particularly a small peptide, frequently modulates the biological activity of the therapeutic agent in a deleterious manner. This loss of both activity and therapeutic usefulness is often the case with lower molecular weight (e.g., less than 4,000 daltons) peptides which have few attachment sites not associated with bioactivity. While the prior art may teach conjugating therapeutic agents to a water-soluble polymer, the prior art fails to teach a conjugate comprising a polymer attached to two or more molecules of synthetic peptide, wherein the conjugate retains substantial bioactivity (e.g., retains substantial biological activity as compared to synthetic peptide alone), and durability (substantial biological activity against a strain of HIV-1 resistant to a synthetic peptide not in the form of a conjugate, as compared to that of the synthetic peptide).

Thus, there is a need for conjugates which can interfere with the interaction of the various domains of gp41 involved in the viral fusion process, and more preferably with the conformational changes of gp41 necessary to effect fusion, thereby inhibiting the fusion of HIV gp41 to a target cell membrane. Additionally, there is a need for conjugates that can inhibit transmission of HIV to a target cell, while retaining substantial biological activity and exhibiting durability. The present invention addresses these needs.

SUMMARY OF THE INVENTION

There is provided, in accordance with the present invention, a conjugate comprising a polymer to which is attached two or more synthetic peptides derived from the HR region of gp41 (HR1 region, HR2 region, or a combination thereof), and which offers the advantages of retaining substantial biological activity (i.e., antiviral activity against HIV), and exhibiting durability (as compared to the synthetic peptide alone (e.g., without being part of a conjugate)). Other features, such as increasing the biological half-life of synthetic peptide which is part of the conjugate (e.g., enabling the synthetic peptide to survive longer in vivo before being degraded in and/or removed from the bloodstream as compared to synthetic peptide alone), will be apparent to one skilled in the art from the descriptions herein. The conjugate according to the present invention may further comprise a pharmaceutically acceptable carrier.

Moreover, the present invention extends to a method of using the conjugate according to the present invention for inhibition of transmission of HIV to a target cell, comprising adding to the virus and the cell an amount of conjugate according to the present invention effective to inhibit infection of the cell by the virus. This method may be used to treat HIV-infected individuals. In a preferred embodiment, inhibiting transmission of HIV to a target cell comprises inhibiting gp41-mediated fusion of HIV-1 to a target cell.

The present invention further extends to methods of making the conjugates according to the present invention. One such method disclosed herein comprises the steps of: (a) reacting a first molecule of synthetic peptide with a polymer to form an intermediate comprising a first intermediate wherein the first molecule of synthetic peptide operably binds to a first reactive functionality of the polymer; (b) reacting the intermediate comprising the first intermediate with a second molecule of synthetic peptide to form a conjugate, wherein the second molecule of synthetic peptide operably binds to the intermediate comprising the first intermediate via a second reactive functionality of the polymer. It will be apparent to one skilled in the art that this method may also comprise adding a plurality of molecules of synthetic peptide simultaneously to a polymer, wherein more than one molecule of synthetic peptide becomes operably bound to the polymer in forming a conjugate, wherein each molecule of synthetic peptide that becomes operably bound is operably bound to a reactive functionality of the polymer.

The above and other objects, features, and advantages of the present invention will be apparent in the following Detailed Description of the Invention when read in conjunction with accompanying drawings.

BRIEF DESCRIPTION OF THE DRAWINGS

FIG. 1 is a schematic of HIV-1 gp41 showing the heptad repeat 1 region (HR1) and heptad repeat 2 region (HR2) along with other functional regions of gp41. Exemplary amino acid sequences corresponding to HR1 and HR2, and the amino acid position numbering, are shown for purposes of illustration and in relation to gp160, strain $HIV_{IIIB}$.

FIG. 2 is a schematic illustration of an embodiment of synthesis of a conjugate according to the present invention.

FIG. 3 is a schematic illustration of another embodiment of synthesis of a conjugate according to the present invention.

DETAILED DESCRIPTION OF THE INVENTION

Definitions:

The terms "first", "second", "third" and the like, may be used herein to: (a) indicate an order; or (b) to distinguish between molecules (e.g., synthetic peptides or intermediates or conjugates which differ in composition compared to one another); or (c) a combination of (a) and (b). However, the terms "first", "second", "third" and the like, are not otherwise to be construed as limiting the invention.

By the term "operably bound" (and tenses thereof) is meant, for purposes of the specification and claims, to refer to fusion or bond or an association of sufficient stability to withstand conditions encountered in vivo for a polymer to remain attached to two or more molecules of synthetic peptide for a sufficient time to increase the biological half-life (as compared to that of synthetic peptide alone) of synthetic peptide which is part of the conjugate according to the present invention. As known to those skilled in the art, the bond may comprise one or more of covalent, ionic, hydrogen, van der Waals, electrostatic, and the like. As known to those skilled in the art, and as will be more apparent by the following embodiments, there are several methods and compositions in which two or more molecules may be operably bound utilizing reactive functionalities. As described herein in more detail, reactive functionalities include, but are not limited to, free chemical groups (e.g., thiol, or carboxyl, hydroxyl, amine, sulfo, etc.), and reactive chemical groups (reactive with free chemical groups).

The term "individual", when used herein for purposes of the specification and claims, means a mammal, and preferably a human.

The term "target cell", when used herein for purposes of the specification and claims, means a cell capable of being infected by HIV. Preferably, the cell is a human cell or are human cells; and more preferably, human cells capable of being infected by HIV via a process including membrane fusion.

The term "pharmaceutically acceptable carrier", when used herein for purposes of the specification and claims, means a carrier medium that does not significantly alter the biological activity of the active ingredient (e.g., a conjugate according to the present invention, or a compound discovered according to a method of the present invention) to which it is added. As known to those skilled in the art, a suitable pharmaceutically acceptable carrier may comprise one or substances, including but not limited to, water, buffered water, saline, 0.3% glycine, aqueous alcohols, isotonic aqueous buffer; and may further include one or more substances such as glycerol, oils, salts such as sodium, potassium, magnesium and ammonium, phosphonates, carbonate esters, fatty acids, saccharides, polysaccharides, glycoproteins (for enhanced stability), excipients, and preservatives and/or stabilizers (to increase shelf-life or as necessary and suitable for manufacture and distribution of the composition). Preferably, the carrier is suitable for intravenous, intramuscular, subcutaneous or parenteral administration (e.g., by injection).

By the term "amino acid" is meant, for purposes of the specification and claims and in reference to the synthetic peptides according to the present invention, to refer to a molecule that has at least one free amine group and at least one free carboxyl group. The amino acid may have more than one free amine group, or more than one free carboxyl group, or may further comprise one or more free chemical reactive groups other than an amine or a carboxyl group (e.g., a hydroxyl, a sulfhydryl, etc.). The amino acid may be a naturally occurring amino acid (e.g., L-amino acid), a non-naturally occurring amino acid (e.g., D-amino acid), a synthetic amino acid, a modified amino acid, an amino acid derivative, an amino acid precursor, and a conservative substitution. One skilled in the art would know that the choice of amino acids incorporated into a peptide will depend, in part, on the specific physical, chemical or biological characteristics required of the antiviral peptide. For example, the skilled artisan would know from the descriptions herein that amino acids in a synthetic peptide may be comprised of one or more of naturally occurring (L)-amino acid and non-naturally occurring (D)-amino acid. A preferred amino acid may be used to the exclusion of amino acids other than the preferred amino acid.

An "amino acid substitution", in relation to amino acid sequence of a synthetic peptide provided with the present invention, is a term used hereinafter for the purposes of the specification and claims to mean one or more amino acids substitution in the sequence of the synthetic peptide such that the ability to bind an HR region of HIV gp41 and inhibit gp41-mediated fusion is substantially unchanged (i.e., as can be measured by antiviral activity in exhibiting an IC50 in the ng/ml range or µg/ml range, as illustrated herein in more detail). Typically, the number of amino acid substitutions ranges from about 1 amino acid to about 10 amino acids in the synthetic peptide, and more preferably from 1 amino acid to about 5 amino acids in the synthetic peptide. As known in the art, the amino acid substitution may comprise a "conservative substitution" which is defined by aforementioned function, and includes substitutions of amino acids having substantially the same charge, size, hydrophilicity, and/or aromaticity as the amino acid replaced. Such conservative substitutions are known to those of ordinary skill in the art to include, but are not limited to, glycine-alanine-valine; isoleucine-leucine; tryptophan-tyrosine; aspartic acid-glutamic acid; arginine-lysine; asparagine-glutamine; and serine-threonine. An amino substitution may also comprise polymorphisms at the various amino acid positions along the HR1 region or HR2 region, depending on which region the synthetic peptide is derived, found in laboratory and/or clinical isolates of HIV. Such polymorphisms are readily available from public gene databases such as GenBank, and other publicly available database of HIV amino acid sequences.

The term "reactive functionality", when used herein for purposes of the specification and claims, means a chemical group or chemical moiety that is capable of forming a covalent bond or bond for operably binding polymer to synthetic peptide. With respect to chemical groups, a reactive functionality is known to those skilled in the art to comprise a group that includes, but is not limited to, maleimide, thiol, carboxy, phosphoryl, acyl, hydroxyl, acetyl, hydrophobic, amido, dansyl, sulfo, a succinimide, a thiol-reactive, an amino-reactive, a carboxyl-reactive, and the like. A chemical moiety may comprise a linker. Linkers are known to refer to a compound or moiety that acts as a molecular bridge to operably link two different molecules (e.g., a wherein one portion of the linker binds to a synthetic peptide, and wherein another portion of the linker binds to the polymer in forming the conjugate according to the present invention). The two different molecules may be linked to the linker in a step-wise manner. There is no particular size or content limitations for the linker so long as it can fulfill its purpose as a molecular bridge. Linkers are known to those skilled in the art to include, but are not limited to, chemical chains, chemical compounds (e.g., reagents), amino acids, and the like. The linkers may include, but are not limited to, homobifunctional linkers, hetero-bifunctional linkers, biostable linkers, and biodegradable linkers, as well known in the art. Preferably, when a linker is used, it is a non-planar (e.g., so that operably bound synthetic peptide is not rigidly fixed to polymer). Heterobifunctional linkers, well known to those skilled in the art, contain one end having a first reactive functionality to specifically link a first molecule, and an opposite end having a second reactive functionality to specifically link to a second molecule. It will be evident to those skilled in the art that a variety of bifunctional or polyfunctional reagents, both homo- and hetero-functional (such as those described in the catalog of the Pierce Chemical Co., Rockford, Ill.), may be employed as a linker with respect to the present invention. Depending on such factors as the molecules to be linked, and the conditions in which the linking is performed, the linker may vary in length and composition for optimizing such properties as preservation of biological function stability, resistance to certain chemical and/or temperature parameters, and of sufficient stereo-selectivity or size. For example, the linker should not significantly interfere with the ability of the synthetic peptide (to which it is linked) to function as an inhibitor of either or both of HIV fusion and HIV transmission to a target cell. A preferred reactive functionality may be used, in application to the present invention, to the exclusion of a reactive functionality other than the preferred reactive functionality.

The term "polymer", when used herein for purposes of the specification and claims, encompasses both homopolymers and copolymers, and further may have a structure comprising a branched structure or linear structure as known to those skilled in the art. Preferably, the polymer is a water-soluble polymer; and more preferably a water-soluble polymer which is substantially non-toxic when used for in vivo applications in individuals. Illustrative examples of such water-soluble polymers include, but are not limited to, polyols, polyethylene glycol ("PEG"), polypropylene glycol ("PPG"), dextran, carboxymethylcellulose, polyvinyl alcohol, polyvinyl pyrrolidone, poly-1,3-dioxolane, poly-1,3,6-trioxane, polyaminoacids (homopolymers, e.g., polylysines, or heteropolymers, e.g., poly(D-L-alanine)-poly(L-lysine)), poly(alkylene oxides), copolymers of ethylene glycol/PPG, copolymers of PEG and an amino acid, copolymers of PEG/thiomalic acid, copolymers of polypropylene oxide/ethylene oxide. Preferably, the polymer used is a discrete species; i.e., each molecule being comprised of the same number of polymer units (e.g., 6 ethylene units in a PEG), rather than a mixture of polymer species with each species having a different size than the other species. For purposes of the present invention, a "polymer" may also comprise a branched or straight chain alkyl (as will be more apparent herein; see, e.g., Table 5). While the polymer used to make the conjugate of the present invention can have a molecular weight in a vast range of molecular weights, in a preferred embodiment the polymer has a molecular weight in the range of about 200 daltons to about 100,000 daltons; and in a more preferred embodiment, the polymer has a molecular size range of from about 300 daltons to about 20,000 daltons. Numerous reactive functionalities can be attached to or made a part of a polymer to which is operably bound a synthetic peptide, and more than one type of reactive functionality may be available on the polymer for selectively binding synthetic peptide (e.g., each type of reactive functionality being available to operably bind a molecule of synthetic peptide, wherein each molecule of synthetic peptide may be the same sequence or differ in sequence from other molecule(s) of synthetic peptide to be bound).

Examples of such reactive functionalities have been previously described herein, and additional examples may include, but are not limited to, ketones, esters, carboxylic acids, aldehydes, alcohols, amines, and the like. In that regard, a polymer may be suitably constructed, modified, or appropriately functionalized using standard organic chemistry techniques to create or expose the reactive functionalities of the polymer which may be used for operably binding to two or more molecules of synthetic peptide in forming a conjugate according to the present invention. Since numerous water-soluble polymers and numerous reactive functionalities have applications in the present invention, the methods of chemical synthesis to make or attach the reactive functionality are dependent on the polymer and the reactive functionality one desires to have on the polymer. Preferably, a polymer for application with the present invention has the following characteristics: (a) is water-soluble, and preferably soluble in aqueous systems such as those typically found in vivo; (b) has more than one reactive functionality (either of the same type or different type; e.g., as to chemical make-up), wherein two or more molecules of synthetic peptide can be operably bound to the polymer via the more than one reactive functionality of the polymer (preferably, each reactive functionality of the polymer desired to be used for operably binding synthetic peptide can operably bind to a reactive functionality of a single molecule of synthetic peptide); and (c) when operably bound to synthetic peptide in forming a conjugate according to the present invention, does not substantially interfere with the biological activity (e.g., antiviral activity) of the synthetic peptide, as can be determined by methods for assessing antiviral activity in vitro and/or in vivo as will be described in more detail herein. A preferred polymer for application in the present invention comprises a polyol, and a more preferred polymer for application in the present invention comprises PEG. A preferred polymer may be applied to the present invention to the exclusion of a polymer other than the preferred polymer.

The term "durability", in relation to a conjugate of the present invention, is used herein for the purposes of the specification and claims to mean that the conjugate demonstrates more potent antiviral activity against HIV-1 strains resistant to one or more synthetic peptides alone (monomer which is unattached to polymer), as compared the antiviral activity of the synthetic peptide alone (as will be more apparent from the descriptions herein). Preferably, durability of the conjugate comprises antiviral activity against such HIV-1 resistant strains, as measured by an IC50 or EC50 of less than (e.g., in the ng/ml) or equal to 1 µg/ml (relative to synthetic peptide) (see, e.g., Table 5).

The term "synthetic peptide", in relation to a peptide used with the present invention, is used herein for the purposes of the specification and claims to mean peptide (a) produced by chemical synthesis, recombinant expression, biochemical or enzymatic fragmentation of a larger molecule, chemical cleavage of larger molecule, a combination of the foregoing or, in general, made by any other method in the art, and isolated; (b) comprising an amino acid sequence of no less than about 16 amino acids and no more than about 60 amino acid residues in length, and consists of no less than 14 contiguous amino acids found in of either the HR1 region or HR2 region of gp41 of HIV (in which may include one or more amino acid substitutions); and (c) capable of inhibiting transmission of HIV to a target cell (preferably, by complexing to either an HR region of HIV gp41 and/or preventing fusion between HIV-1 and a target cell), as can be determined by assessing antiviral activity in vitro and/or in vivo as will be described in more detail herein. The term "isolated" when used in reference to a peptide, means that the synthetic peptide is substantially free of components which have not become part of the integral structure of the peptide itself; e.g., such as substantially free of cellular material or culture medium when produced by recombinant techniques, or substantially free of chemical precursors or other chemicals when chemically synthesized or produced using biochemical or chemical processes. The amino acid sequence of the synthetic peptide may comprise one or more amino acid substitutions and/or one or polymorphisms found in the sequence of the relevant region of the HIV gp41, or may comprise one or more amino acid substitutions which are added to stabilize helix structure and/or affect oligomerization so that the peptide self-assembles into a trimer (see, for example, the disclosure of U.S. application Ser. No. 10/664,021 which is herein incorporated by reference). Further, the amino acid sequence, in addition to having a core peptide derived from HIV gp41, may comprise one or more enhancers peptides linked to the core peptide, e.g., at the N-terminus, at the C-terminus or at both the N-terminus and C-terminus, or may have a core peptide derived from one or more of HIV-1, HIV-2, and SIV (see, e.g., U.S. Pat. No. 6,258,782, the disclosure of which is herein incorporated by reference; see also synthetic peptide comprising the amino acid sequences shown in SEQ ID NOs:5, & 46 to 59). Depending on the synthetic peptide used, the synthetic peptide operably bound to polymer may exist as a monomer, or an oligomeric form such as a trimer. In an example wherein the synthetic peptide exists as a trimer, only a single molecule may be operably bound to the polymer, whereas the rest of the molecules of synthetic peptide comprising the trimer are self-assembled around the operably bound molecule of synthetic peptide. For example, illustrative synthetic peptides comprising HR1 peptides having amino acid substitutions therein (compared to SEQ ID NO:1) which preferably self-assemble into trimers (e.g., a trimer being comprised of three molecules of synthetic peptide) comprise the amino acid sequences shown in SEQ ID NOs:61 to 74. Preferably, the synthetic peptide for application to the present invention may comprise a sequence of no less than about 16 amino acids and no more than about 60 amino acid residues in length, and preferably no less than 36 amino acids and no more than about 51 amino acids in length, and more preferably no less than about 41 amino acids and no more than about 51 amino acids in length. Preferably, for a synthetic peptide comprising sequence derived from the HR1 region of HIV gp41, the synthetic peptide comprises a contiguous sequence of at least amino acid residues 18 to 54 of SEQ ID NO:1 (by single letter designation, NNLL-RAIEAQQHLLQL TVWGIKQLQARILAVERYL KD) or polymorphisms thereof, as key determinants in this portion of the HR1 region have been found to influence biochemical and antiviral parameters described herein. Illustrative synthetic peptides derived from the HR1 region include, but are not limited to peptides having the amino acid sequences shown in SEQ ID NOs:3, & 6 to 31. A preferred synthetic peptide derived from the HR1 region may be used in producing a conjugate according to the present invention to the exclusion of an HR1 peptide other than the preferred synthetic peptide. Preferably, for a synthetic peptide sequence derived from the HR2 region of HIV gp41, the synthetic peptide comprises a contiguous sequence of at least amino acid residues 43 to 51 of SEQ ID NO:2 (e.g., QQEKNEQEL), as key determinants in this portion of the HR2 region have been found to influence biochemical and antiviral parameters described herein. Illustrative synthetic peptides derived from the HR2 region include, but are not limited to peptides having the amino acid sequences shown in SEQ ID NOs:4, 32, 75 to 99, & 114. A preferred synthetic peptide derived from the HR2 region may be used in producing a conjugate according to the present invention to the exclusion of an HR2 peptide other than the preferred synthetic peptide. Numerous of such synthetic peptides that may be applied to the present invention have been disclosed previously in, for example, U.S. Pat. Nos. 5,656,480, 6,133,418, and 6,258,782; the disclosures of which are herein incorporated by reference in their entirety). The term "synthetic peptide alone" is used herein, for the purposes of the specification and claims, to mean synthetic peptide not operably bound to polymer; i.e., in an unconjugated form which is devoid of polymer.

The present invention is illustrated in the following examples, which are not intended to be limiting.

EXAMPLE 1

The embodiment illustrates a method of making the conjugates according to the present invention. One such method disclosed herein comprises the steps of: (a) reacting a first molecule of synthetic peptide with a polymer to form an intermediate comprising a first intermediate wherein the first molecule of synthetic peptide operably binds to a first reactive functionality of the polymer; (b) reacting the intermediate comprising a first intermediate with a second molecule of synthetic peptide to form a conjugate, wherein the second molecule of synthetic peptide operably binds to the intermediate comprising the first intermediate via a second reactive functionality of the polymer. It will be apparent to one skilled in the art that this method may also comprise adding a plurality of molecules of synthetic peptide simultaneously to a polymer, wherein more than one molecule of synthetic peptide becomes operably bound to the polymer in forming a conjugate, wherein each molecule of synthetic peptide that becomes operably bound is operably bound to a reactive functionality of the polymer.

Peptides were synthesized on a peptide synthesizer using standard solid-phase synthesis techniques and using standard FMOC peptide chemistry (see also, U.S. Pat. No. 6,015,881, assigned to the present assignee). In this example, the synthetic peptides further comprised reactive functionalities; i.e., were blocked at the N-terminus by an acetyl group and at the C-terminus by an amide group. After cleavage from the resin, the peptides were precipitated, and the precipitate as lyophilized. The peptides were then purified using reverse-phase high performance liquid chromatography; and peptide identity was confirmed with electrospray mass spectrometry. In this example, T20 (SEQ ID NO: 4) was used to operably bind to polymer in making a conjugate according to the present invention. As previously described herein in detail, because of essentially the same mechanism of action (in inhibiting fusion), because constructed of similar basic units (heptads and leucine zipper-like motifs), and because of similar conformational structure (alpha helix and coiled coils), conjugates comprised of synthetic peptide other than T20 (SEQ ID NO:4), whether derived from the HR1 region or HR2 region of HIV-1 gp41, should function comparably to the various conjugates comprised of T20 (SEQ ID NO:4) illustrated herein. Such other synthetic peptides include, but are not limited to, amino acid sequences comprising SEQ ID NOs: 3, 5-99 & 114. Likewise, the same or similar methods may be used to operably bind any synthetic peptide to a polymer. While this example shows one type (e.g., of the same amino acid sequence) of synthetic peptide derived from the HR2 region of HIV gp41, it will be apparent to one skilled in the art from the descriptions herein that more than one type of synthetic peptide may be operably bound to the same molecule of polymer. For example, in making a conjugate comprising no less than two molecules of synthetic peptide operably bound to a molecule of polymer, various other combinations may be applied which include, but are not limited to,: each molecule of synthetic peptide is derived from the HR1 region of HIV gp41, and comprises the same (an identical) amino acid sequence as compared to other synthetic peptide comprising the conjugate; each molecule of synthetic peptide is derived from the HR1 region of HIV gp41, and at least one of the molecules of synthetic peptide differs in amino acid sequence as compared to other synthetic peptide comprising the conjugate (e.g., SEQ ID NO:3 and SEQ ID NO:27 when a conjugate comprises two molecules of synthetic peptide operably bound to a polymer); each molecule of synthetic peptide is derived from the HR2 region of HIV gp41, and comprises the same (an identical) amino acid sequence as compared to other synthetic peptide comprising the conjugate; each molecule of synthetic peptide is derived from the HR2 region of HIV gp41, and at least one of the molecules of synthetic peptide differs in amino acid sequence as compared to other synthetic peptide comprising the conjugate (e.g., SEQ ID NO:4 and SEQ ID NO:5 when a conjugate comprises two molecules of synthetic peptide operably bound to a polymer); or at least one molecule of synthetic peptide comprises an amino acid sequence derived from the HR1 region which self assembles in solution into trimers (e.g., SEQ ID NO:63), and at least one molecule of synthetic peptide comprises an amino acid sequence derived from the HR2 region of HIV gp41 (e.g., SEQ ID NO:4) (this is because a few trimers preferentially bind to some synthetic peptides derived from HR2, and bind less favorably to other synthetic peptides derived from HR2). As apparent to one skilled in the art from the descriptions herein, various combinations of synthetic peptide may also be used when more than two molecules of synthetic peptide are operably bound to a molecule of polymer. The number of molecules of synthetic peptide to operably bind to a molecule of polymer depends on factors which may include, but are not limited to, the polymer size, polymer composition, synthetic peptide composition, and the number of reactive functionalities on the polymer available for operably binding to synthetic peptide. Preferably, the number of molecules of synthetic peptide operably bound to a molecule of polymer is in the range of from 2 to about 20, and more preferably, in a range of from 2 to about 5. Also, as apparent to one skilled in the art, and depending on the reactive functionalities used to operably bind a synthetic peptide to a polymer, the no less than two molecules of synthetic peptide may be operably bound to the polymer via a portion of the synthetic peptide selected from the group consisting of a carboxy terminus (C-terminal end), an amino terminus (N-terminal end), an internal lysine, and a combination thereof (e.g., wherein one molecule of synthetic peptide is operably bound via its C-terminus, and another molecule of synthetic peptide is operably bound by its N-terminus; etc.).

Figure 2:
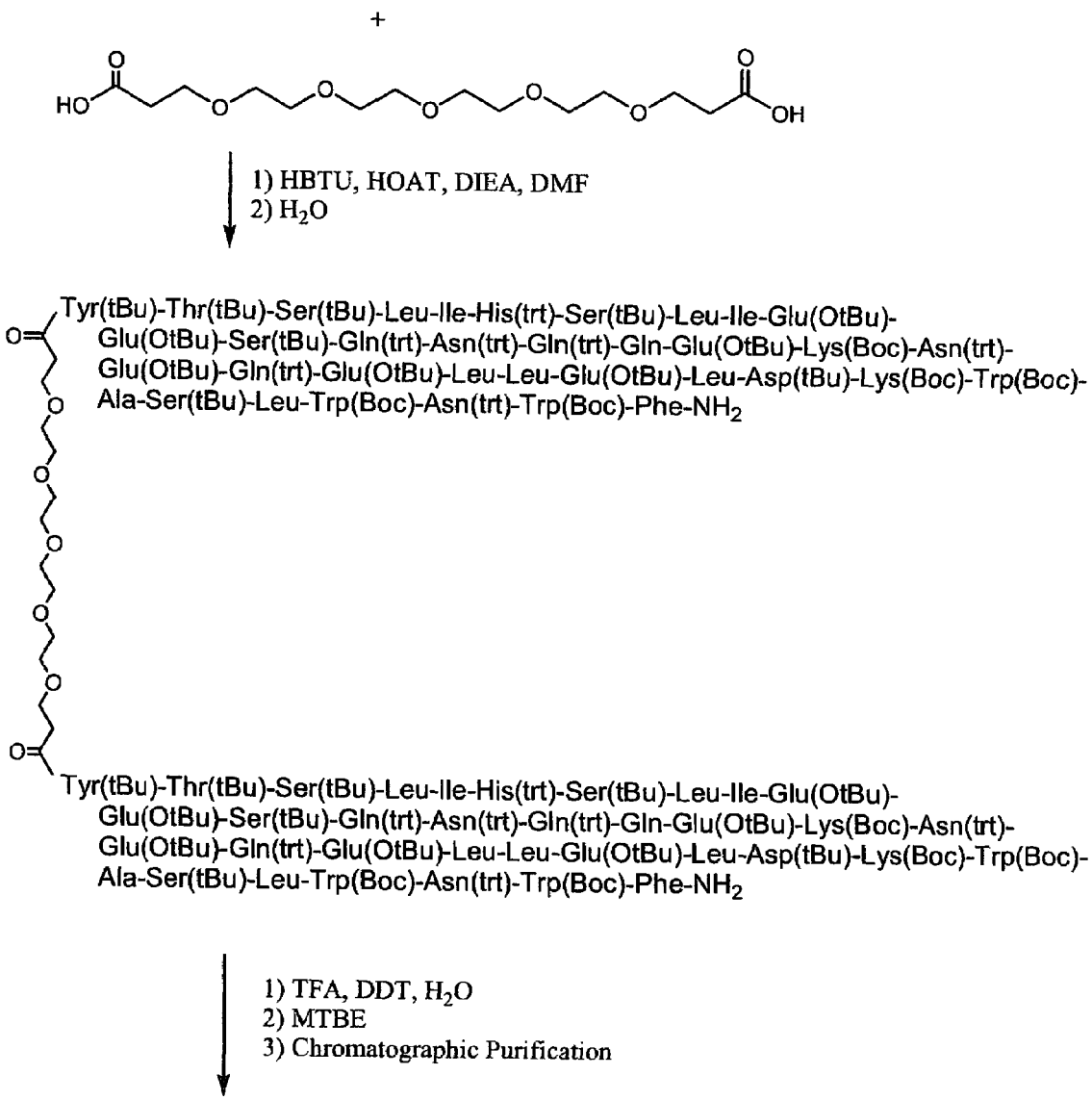
Figure 2:
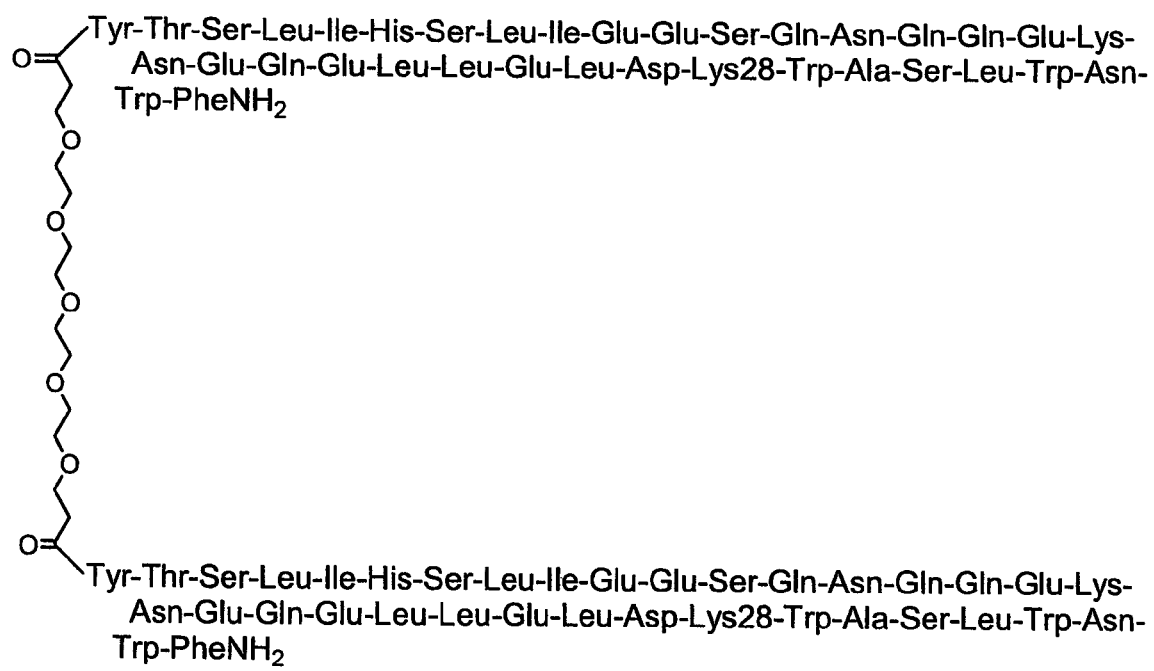

In one illustrative embodiment, and with reference to FIG. 2, a conjugate according to the present invention was produced by operably binding two molecules of T20 (SEQ ID NO:4) via the N-terminus of the synthetic peptide to reactive functionalities of a polymer, PEG. More particularly, a molecule of T20 (SEQ ID NO:4) was operably bound by an amide linkage to an acid of PEG, whereas another molecule of T20 (SEQ ID NO:4) was operably bound by an amide linkage to a second acid of PEG in forming a conjugate comprising T20-PEG dimer. For example, PEG diacid (approximately 300 daltons,11.4 mg, 0.0339 mmole), 7-aza-1-hydroxybenzotriazole (HOAT, 10 mg, 0.0746 mmole) and N,N-diisopropylethylamine (DIEA,13.1 mg, 0.102 mmole) were dissolved in dimethyl-formamide DMF (5 mL) then O-benzotriazol-1-yl-N,N,N', N'-tetramethyluronium tetrafluoroborate (TBTU, 21.8 mg, 0.0678 mmole) was added. The solution was stirred for 5 minutes at ambient temperature and the side-chain protected T20 (500 mg, 0.0678 mmole) was added. The solution was stirred at ambient temperature for 24 hours. Water (15 ml) was added to precipitate the peptide. The solid was collected by vacuum filtration, washed with water (2×5 ml) and dried to give the side-chain protected T20-PEG dimer (487 mg) in 96% yield. The side-chain protected T20-PEG dimer (485 mg) was dissolved in trifluoroacetic acid (TFA, 6.3 ml) containing water (0.35 ml) and dithiothreitol (DTT, 0.35 g) as cation scavengers. The solution was stirred at ambient temperature under an atmosphere of nitrogen for 4 hours. To precipitate the crude T20-PEG dimer, methyl tert-butyl ether (MTBE) was added. The solid was spun down in a centrifuge and the MTBE is decanted to waste. The MTBE wash cycle was repeated twice. The solid was dissolved in 3:1 water/ACN (acetonitrile, 40 mL) and the pH was adjusted to 6-7 with ammonium hydroxide. The pH of the solution was lowered to pH 4 to 5 by adding acetic acid (0.5 ml). The resulting turbid solution was allowed to stand at ambient temperature overnight to complete the side-chain deprotection. The slurry was adjusted to pH 7 to 8 to get all the solids back into solution, then frozen, and then lyophilized to yield crude T20-PEG dimer (375 mg). The crude T20-PEG dimer was purified by high performance liquid chromatography (HPLC) using C18, 5 micron reverse phase packing as the stationary phase and acetonitrile/water with 0.1% TFA as the mobile phase (40-50% organic over 90 minutes). The pure, product containing fractions were pooled, frozen and lyophilized to give 40 mg of conjugate (89.8A% by HPLC, MS found 9196.545, calculated 9196.489).

While this illustrative example describes operably binding the N-terminus of synthetic peptide to the polymer, it will be apparent to one skilled in the art that a number of different approaches may be used to operably bind synthetic peptide to polymer. For example, the carboxyl terminus of the synthetic peptide may be operably linked to polymer using standard methods known in the art (e.g., the carboxyl terminus of synthetic peptide having a terminal amine is operably bound to PEG carboxylic acid). In another example, an internal lysine (via an amine reactive functionality) of synthetic peptide is operably bound to polymer using methods known in the art (e.g., activation of PEG using the active ester method with N-hydroxylsuccinimide, modifying the amino group in the side chain of a lysine residue internal to the amino acid sequence of the synthetic peptide).

Figure 3:
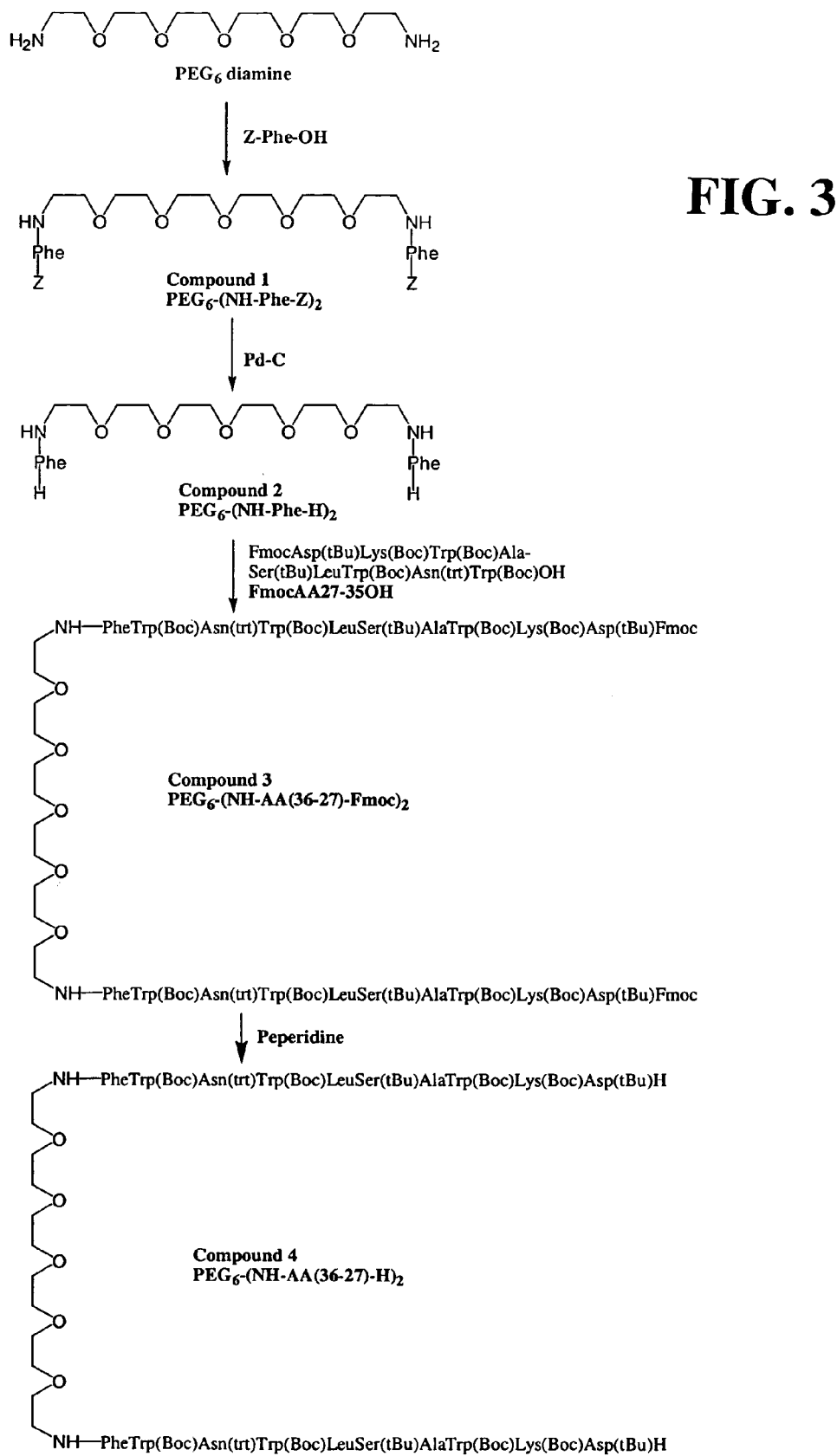
Figure 3:
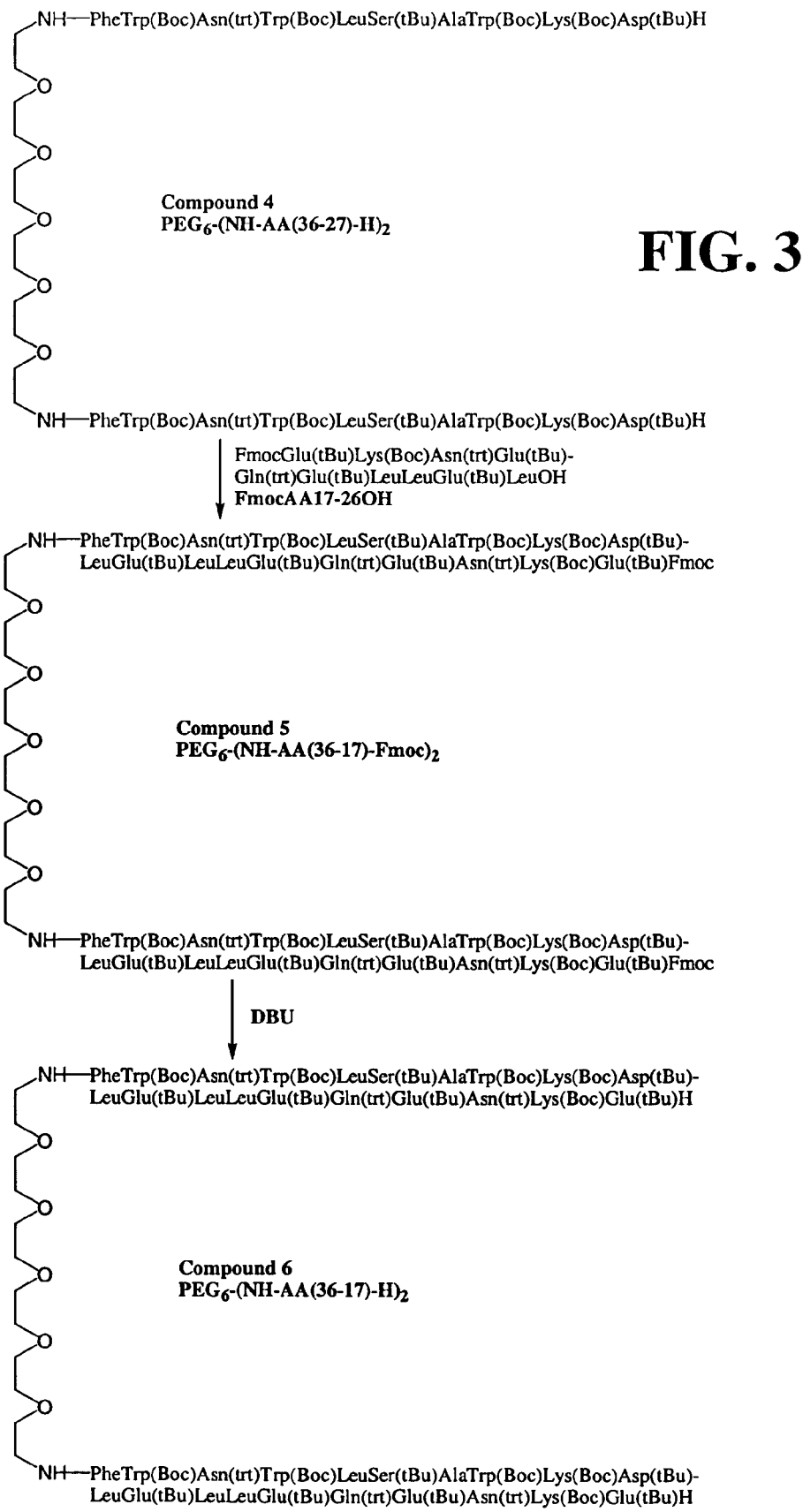
Figure 3:
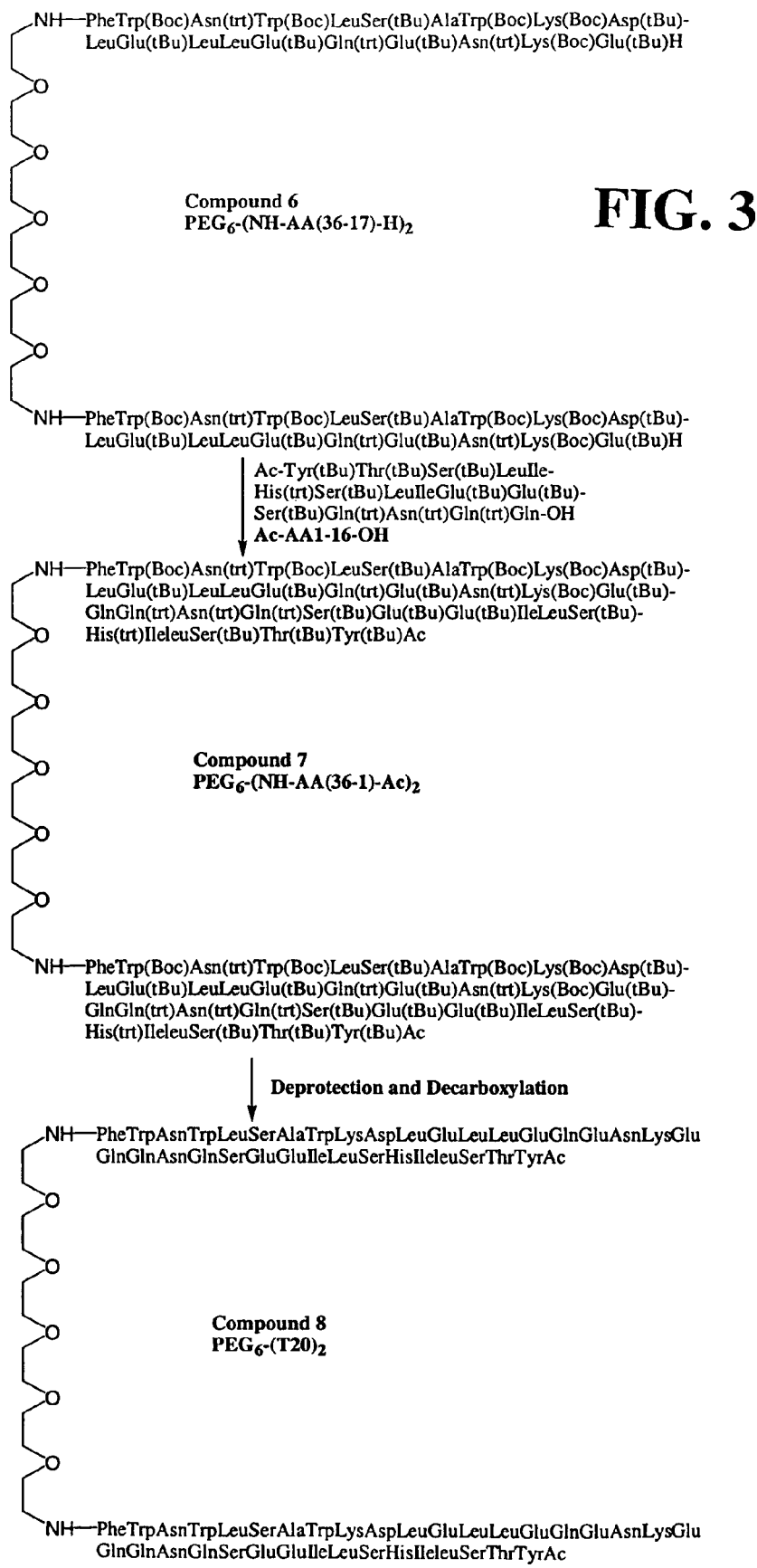

For example, synthetic peptide was operably bound to polymer via the C-terminus of the synthetic peptide in forming a conjugate according to the present invention. More particularly, two molecules of synthetic peptide (T20, SEQ ID. NO:4) were operably linked through their respective reactive functionality to $PEG_6$ diamine in a series of synthesis steps as illustrated in FIG. 3.

Step 1. Formation of $PEG_6$-(NH-Phe-Z)$_2$

A 50-ml round bottom flask equipped with a magnetic stirrer was charged with Z-Phe-OH (0.43 g, 1.43 mmol, 2 eq), 6-Cl-HOBT (0.27 g, 1.57 mmol, 2.2 eq), acetonitrile (6 ml) and DIEA (0.37 ml, 2.14 mmol, 3 eq). The resulting yellow solution was cooled by ice bath at 0 to 5° C. and then HBTU (0.60 g, 1.57 mmol, 2.2 eq) was added in. To the above solution was $PEG_6$ diamine (0.20 g, 0.714 mmol, 1.0 eq) added by $CH_2Cl_2$ (2 ml×2). The reaction mixture was stirred at 0 to 5° C. for 15 minutes and then warmed to room temperature and stirred for another 1.5 hours. The reaction mixture was transferred to a 125-ml separatory funnel by $CH_2Cl_2$ (10 ml×3) and washed by $NaHCO_3$ solution (0.33M, 15 ml×3) and NaCl solution (15 ml). The organic phase was dried over $MgSO_4$ and filtered. The residue after removal of the solvent was applied to silica gel column which was deactivated by 10% $Et_3N$ in Hexane. The desired product was eluted out by $CH_2Cl_2$-MeOH (20:1). Removal of the solvent afforded compound 1, $PEG_6$-(NH-Phe-Z)$_2$, as a colorless oil (0.23 g, 40%).

Step 2. Formation of $PEG_6$-(NH-Phe-H)$_2$

A 50-ml round bottom flask equipped with a magnetic stirrer was charged with compound 1, $PEG_6$-(NH-Phe-Z)$_2$, (0.20 g, 0.24 mmol), 10% Pd—C (dry, 50 mg) and MeOH (10 ml). The reactor was degassed by $N_2/H_2$twice before the hydrogenation at room temperature with $H_2$ balloon for overnight. Pd—C was filtered off and the solvent was removed to give compound 2, $PEG_6$-(NH-Phe-H)$_2$, as a colorless oil (0.13 g, 95%).

Step 3. Formation of $PEG_6$-(NH-AA(36-27)-Fmoc)$_2$

Note AA 36-27 refers to amino acids 36 to 27 of SEQ ID NO:4. A 100-ml round bottom flask equipped with a magnetic stirrer was charged with compound 2, $PEG_6$-(NH-Phe-H)$_2$, (0.44 g, 0.76 mmol, 1 eq), Fmoc-AA(27-35)-OH (3.34 g, 1.53 mmol, 2 eq), HOAT (0.31 g, 2.3 mmol, 3.0 eq), DIEA (0.53 ml, 3.1 mmol, 4 eq) and DMF (20 ml). The resulting yellow solution was cooled by ice bath at 0 to 5° C. and then HBTU (0.61 g, 1.61 mmol, 2.1 eq) was added in. The reaction mixture was stirred at 0 to 5° C. for 10 minutes and then warmed to room temperature and stirred for 3 hours. $H_2O$ (30 ml) was added into the reaction mixture with ice bath and the resulted white slurry was stirred for 30 minutes before vacuum filtration. The white solid was washed by $H_2O$ (30 ml) and dried in vacuum oven (35° C.) for overnight. (3.85 g, crude compound 3, $PEG_6$-(NH-AA(36-27)-Fmoc)$_2$)

Step 4. Formation of $PEG_6$-(NH-AA(36-27)-H)$_2$

To the solution of crude compound 3, $PEG_6$-(NH-AA(36-27)-Fmoc)$_2$, (3.30 g, 0.67 mmol) in DMF (10 ml) was added piperidine (0.53 ml, 5.4 mmol, 8 eq). After stirring at room temperature for 4 hours, the reaction mixture was cooled by ice bath and $H_2O$ (15 ml) was added in. The resulting white slurry was stirred for 20 minutes before the filtration. The white solid was washed by MTBE-Heptane (1:1, 25 ml×2), and then was transferred back to a 100-ml flask and triturated with EtOH—$H_2O$ (1:1, 10 ml). The solid was collected by vacuum filtration and washed by EtOH—$H_2O$ (1:1, 20 ml). The filtration and washing with EtOH—$H_2O$ was repeated once. The crude compound 4, $PEG_6$-(NH-AA(36-27)-H)$_2$, was dried in vacuum oven (35° C.) for overnight (2.53 g).

Step 5. Formation of $PEG_6$-(NH-AA(36-17)-Fmoc)$_2$

Note, in this step was added amino acids 26 to 17 of SEQ ID NO:4. A 100-ml round bottom flask equipped with a magnetic stirrer was charged with compound 4, $PEG_6$-(NH-AA(36-27)-H)$_2$, (1.82 g, 0.41 mmol, 1 eq), Fmoc-AA(17-26)-OH (1.87 g, 0.82 mmol, 2 eq), HOAT (0.17 g, 1.23 mmol, 3.0 eq), DIEA (0.31 ml, 1.64 mmol, 4 eq) and DMF (25 ml). The resulting yellow solution was cooled by ice bath at 0 to 5° C. and then HBTU (0.33 g, 0.86 mmol, 2.1 eq) was added in. The reaction mixture was stirred at 0 to 5° C. for 15 minutes and then warmed to room temperature and stirred for 3 hours. $H_2O$ (30 ml) was added into the reaction mixture with ice bath and the resulted white slurry was stirred for 30 minutes before vacuum filtration. The white solid was washed by $H_2O$ (30 ml) and then returned to a 100-ml flask charged with IPA-$H_2O$ (95:5, 20 ml). The mixture was heated to 60° C. for 5 minutes and gradually cooled down to room temperature. The solid was collected by vacuum filtration and washed by IPA (5 ml×4). The crude compound 5, PEG$_6$-(NH-AA(36-17)-Fmoc)$_2$, was dried on the funnel under vacuum (4.4 g, not completely dry).

Step 6. Formation of PEG$_6$-(NH-AA(36-17)-H)$_2$

To the solution of crude compound 5, PEG$_6$-(NH-AA(36-17)-Fmoc)$_2$, (3.0 g, not dry) in NMP (10 ml) was DBU (100 μl) added. After stirring at room temperature for 1 hr, PL-SO$_3$H resin (150 mg) was added in and continued stirring for 40 minutes. The resin was filtered off and washed by NMP (10 ml). The treatment of the NMP solution with H$_2$O (30 ml) resulted in a milk-like emulsion. H$_2$O (100 ml) was added to the emulsion and the mixture was then lyophilized. The resulting yellow sticky oil was suspend with EtOH (10 ml), heated to 50° C. for 5 minutes, and then cooled down to room temperature. The white slurry was formed upon the addition of H$_2$O (20 ml) and stirred for 30 minutes. The white solid was collected by vacuum filtration and washed by EtOH—H$_2$O (1:1, 10 ml×2). The crude compound 6, PEG$_6$-(NH-AA(36-17)-H)$_2$, was dried in vacuum oven (35° C.) for overnight.

Step 7. Formation of PEG$_6$-(NH-AA(36-1)-Ac)$_2$

Note in this step, added were amino acids 16 to 1 of SEQ ID. NO:4. A 50-ml round bottom flask equipped with a magnetic stirrer was charged with compound 6, PEG$_6$-(NH-AA(36-17)-H)$_2$, (0.48 g, 0.056 mmol,1 eq), Fmoc-AA(1-16)-Ac (0.37 g, 0.112 mmol, 2 eq), HOAT (0.023 g, 0.169 mmol, 3.0 eq), DIEA (0.040 ml, 0.225 mmol, 4 eq) and DMF (5 ml). The resulting yellow solution was cooled by ice bath at 0 to 5° C. and then HBTU (0.047 g, 0.124 mmol, 2.2 eq) was added in. The reaction mixture was stirred at 0 to 5° C. for 15 minutes and then warmed to room temperature and stirred for 3 hours. H$_2$O (30 ml) was added into the reaction mixture while in an ice bath, and the resulted white slurry was stirred for 30 minutes before vacuum filtration. The white solid was washed by H$_2$O (30 ml) and then returned to a 50-ml flask and triturated with MeCN—H$_2$O (9:1). The solid was collected by vacuum filtration and washed by H$_2$O (10 ml×2). The crude compound 7, PEG$_6$-(NH-AA(36-1)-Ac)$_2$ was dried on the funnel under vacuum (0.73 g, not completely dry).

Step 8. Formation of PEG$_6$-(T20)$_2$

A 25-ml flask with the crude compound 7, PEG$_6$-(NH-AA(36-1)-Ac)$_2$, (0.20 g) was charged with TFA/DTT/H$_2$O (90:5:5, 2.5 ml). The resulting yellow solution was stirred at room temperature for 2 hours. To the cooled reaction mixture by ice-bath was MTBE (8 ml) added and the resulting slurry was stirred for 20 minutes before vacuum filtration. The yellow solid was washed by MTBE (5 ml×2) and dried on the funnel under vacuum for 30 minutes (not completely dry). The yellow solid was dissolved in MeCN/H$_2$O (1:1, 1 ml). The resulting yellow suspension was filtered through cotton and washed by MeCN/H$_2$O (1:1, 1 ml×2). The pH value of the combined solution was adjusted to 4 by NaHCO$_3$ solution (0.33N). To the above solution added was HOAc (60 ul), and the light yellow solution was stirred at room temperature for overnight. The pH value of the reaction mixture was adjusted to 8 by K$_2$CO$_3$ solution (1M). The solution was diluted by MeCN—H$_2$O (15:85, 3 ml) and applied to HPLC for separation. (PLRP-XL, 300A, 10 um, 20×300 mm; Buffer A, 100 mM NH$_4$OAc in H$_2$O, pH 8.5, adjusted by NH$_4$OH; Buffer B, MeCN: Gradient, 20% to 40% in 60 min; flow rate, 15 ml/min). The collected fractions were checked by HPLC respectively, and the pure fractions were pooled together for lyophilization. The final product comprising a conjugate according to the present invention (PEG$_6$-(T20)$_2$) was obtained as white powder, 5.5 mg.

EXAMPLE 2

Illustrated in this example is the increased bioavailability (e.g., an extension of circulating half-life in vivo) of a conjugate according to the present invention as compared to the half-life of synthetic peptide alone. Using the methods and compositions taught in Example 1 herein, synthetic peptide and conjugate were produced. It is important to note that standard animal model for determining bioavailability has been correlated with the bioavailability of synthetic peptide in vivo in humans (as described in more detail in U.S. Pat. No. 6,258,782). Briefly, cannulated mice were dosed intravenously with either synthetic peptide, or a conjugate according to the present invention, with the dosing solution concentration being determined using the Edelhoch method, and as adjusted based on animal weight to achieve a 10 mg/kg dose. A sample of blood was removed at predetermined time intervals (0, 15, 30 min and 1, 2, 4, 6, and 8 hours) and added to collection tubes containing anticoagulant (EDTA). Plasma was harvested from each of the collection tubes, and then subjected to analysis by fluorescence high pressure liquid chromatography (HPLC). In addition to sample dilutions, serial dilutions of dosing solution were performed in buffer as well as in plasma, and used to generate a standard curve relating peak area to known concentration of peptide. This curve was then used to calculate concentration of peptide in plasma taking into account all dilutions performed and quantity injected onto column. The half-life (t ½) and total AUC (Area Under Curve) of synthetic peptide alone, and of the conjugate containing synthetic peptide according to the present invention is shown in Table1.

TABLE 1

| | Agent tested | |
| --- | --- | --- |
| | AUC (μg * hr/ml) | t ½ (hours) |
| T20 Peptide | 158 | 1.6 |
| Conjugate | 500 | 4.3 |

As illustrated by the results in Table 1, a conjugate according to the present invention can have a significantly increased (greater than two-fold) circulating half-life as compared to the circulating half-life of synthetic peptide alone.

EXAMPLE 3

Illustrated in this example is the unexpected result of antiviral potency using the conjugates according to the present invention. In using an in vitro assay for demonstrating antiviral potency, it is important to note that antiviral effect of synthetic peptide demonstrated in the in vitro assay has been correlated with the antiviral effect of the synthetic peptide in vivo. In determining antiviral activity (e.g., one measure being the ability to inhibit transmission of HIV to a target cell) of the conjugates according to the present invention, used was an in vitro assay which has been shown, by data generated using synthetic peptides derived from either of the HR regions of HIV gp41, to be predictive of antiviral activity observed in vivo. More particularly, antiviral activity observed using an in vitro infectivity assay ("Magi-CCR5 infectivity assay"; see, e.g., U.S. Pat. No. 6,258,782) has been shown to reasonably correlate to antiviral activity observed in vivo for the same HIV gp41 derived peptides (see, e.g., Kilby et al., 1998, *Nature Med.* 4:1302-1307). To further emphasize this point, T20 (SEQ ID NO:4) and T1249 (SEQ. ID NO:5) each have demonstrated potent antiviral activity against HIV in both the in vitro infectivity assay and human clinical trials.

The infectivity assays score for reduction of infectious virus titer employing the indicator cell lines MAGI or the CCR5 expressing derivative cMAGI. Both cell lines exploit the ability of HIV-1 tat to transactivate the expression of a β-galactosidase reporter gene driven by the HIV-LTR. The β-gal reporter has been modified to localize in the nucleus and can be detected with the X-gal substrate as intense nuclear staining within a few days of infection. The number of stained nuclei can thus be interpreted as equal to the number of infectious virions in the challenge inoculum if there is only one round of infection prior to staining. Infected cells are enumerated using a CCD-imager and both primary and laboratory adapted isolates show a linear relationship between virus input and the number of infected cells visualized by the imager. In the MAGI and cMAGI assays, a 50% reduction in infectious titer (Vn/Vo=0.5) is significant, and provides the primary cutoff value for assessing antiviral activity ("IC50" is defined as the dilution resulting in a 50% reduction in infectious virus titer). A secondary cutoff of Vn/Vo=0.1, corresponding to a 90% reduction in infectious titer is also assessed ("IC90"). Peptides tested for antiviral activity were diluted into various concentrations, and tested in duplicate or triplicate against an HIV inoculum adjusted to yield approximately 1500-2000 infected cells/well of a 48 well microtiter plate. The peptide (in the respective dilution) was added to the cMAGI or MAGI cells, followed by the virus inocula; and 24 hours later, an inhibitor of infection and cell-cell fusion (e.g., T20) was added to prevent secondary rounds of HIV infection and cell-cell virus spread. The cells were cultured for 2 more days, and then fixed and stained with the X-gal substrate to detect HIV-infected cells. The number of infected cells for each control and peptide dilution was determined with the CCD-imager, and then the IC50 and IC90 were calculated (expressed in µg/ml).

In this first example of antiviral potency, two clinical isolates of HIV were obtained from the same HIV-infected individual. A first isolate, hereby designated "HIV-1 T20S" for ease of description, was sensitive to the antiviral effect of T20 (SEQ ID NO:4) both in vitro and in vivo. The second isolate, hereby designated "HIV-1 T20R" for ease of description, exhibited resistant to the antiviral effect of T20 (SEQ ID NO:4) both in vitro and in vivo. The two clinical isolates, HIV-1 T20S and HIV-1 T20R, were used in an in vitro infectivity assay in which the antiviral effect of T20 (SEQ ID NO:4; synthetic peptide alone; Table 2 "T20 Peptide") was compared to a conjugate according to the present invention (e.g., conjugate comprising two molecules of T20 (SEQ ID NO:4) operably bound to PEG; Table 2, "conjugate") and to polymer (e.g., PEG) having one molecule of synthetic peptide (T20) operably bound thereto (Table 2, "PEG-T20-monomer"). The results, with the IC50 expressed in ng/ml, are illustrated in Table 2.

TABLE 2

| | Agent tested | |
|---|---|---|
| | HIV-1 T20S: IC50 | HIV-1 T20R: IC50 |
| T20 Peptide | 10 | 1,211 |
| Conjugate | 32 | 49 |
| PEG-T20 monomer | 1,149 | >20,000 |

Several conclusions can be drawn from the results illustrated in Table 2. First, as shown by the results using the T20-sensitive HIV isolate, conjugate according to the present invention (in which at least two molecules of synthetic peptide are operably bound to a molecule of polymer) retains substantial biological (antiviral) activity as compared to the synthetic peptide alone (e.g., there only a difference of 3 fold and is much less than a log difference). In contrast, as shown by the results using the T20 sensitive isolate, a polymer having only a single molecule of synthetic peptide operably bound thereto (e.g., Table 2, "PEG-T20 monomer") showed a significant change (a log reduction) in biological activity compared to synthetic peptide alone. It was an unexpected result that the retention of biological activity of the conjugate, as compared to the PEG-T20 monomer, was more than could be contributed to an additive effect of the number of molecules of synthetic peptide per compound (e.g., two molecules of synthetic peptide operably bound to polymer versus one molecule of synthetic peptide operably bound to polymer).

Secondly, as shown by the results using the T20-resistant HIV isolate, it was an unexpected result that conjugate according to the present invention showed more potent antiviral activity (at least a log difference) against an HIV isolate that demonstrated resistance to synthetic peptide alone (and that also demonstrated resistance to PEG-T20 monomer). More particularly, it was quite surprising to observe that a conjugate, having two molecules of T20 operably bound thereto, had significant antiviral activity to a T20-resistant HIV isolate (in exhibiting durability). In summarizing the results shown in Table 2, demonstrated is that a conjugate according to the present invention retains substantial biological activity comprising antiviral activity against HIV, and demonstrates durability against HIV resistant strains, as compared to synthetic peptide alone. This biological activity was demonstrated in an in vitro assay which has been correlated with antiviral effects observed in vivo.

To further illustrate the unexpected results that a conjugate according to the present invention showed potent antiviral activity against an HIV isolate that demonstrated resistance to synthetic peptide alone, several other T20-sensitive isolates and T20-resistant isolates (isolates "A-D") were tested using the in vitro infectivity assay, as shown in Table 3. IC50 and IC90 are expressed in µg/ml.

In summarizing the results shown in Table 3, demonstrated is that a conjugate according to the present invention not only retains substantial biological activity comprising antiviral activity against HIV (as compared to synthetic peptide alone), but surprisingly shows durability comprising potent antiviral activity against HIV isolates which are resistant to synthetic peptide alone.

TABLE 3

| Virus | T20 Peptide IC50 | T20 Peptide IC90 | Conjugate IC50 | Conjugate IC90 |
|---|---|---|---|---|
| HIV-1 T20S-A | 0.006 | 0.078 | 0.034 | 0.200 |
| HIV-1 T20R-A | >5 | >5 | 0.330 | 2.524 |
| HIV-1 T20S-B | 0.029 | 0.117 | 0.013 | 0.087 |
| HIV-1 T20R-B | 1.898 | 7.179 | 0.044 | 0.257 |
| HIV-1 T20S-C | 0.006 | 0.073 | 0.024 | 0.151 |
| HIV-1 T20R-C | 1.544 | 6.285 | 0.105 | 0.610 |
| HIV-1 T20S-D | 0.018 | 0.208 | 0.063 | 0.457 |
| HIV-1 T20R-D | 2.039 | >5 | 0.030 | 0.210 |

Additional HIV strains were tested in the in vitro infectivity assay to further illustrate that a conjugate according to the present invention retains substantial biological activity when compared to synthetic peptide alone. With reference to Table 4, IC50 and IC90 are expressed in µg/ml.

TABLE 4

| Virus | T20 Peptide IC50 | T20 Peptide IC90 | Conjugate IC50 | Conjugate IC90 |
|---|---|---|---|---|
| IIIB/CEM4 | 0.007 | 0.052 | 0.035 | 0.206 |
| 3'GIV/CEM4 | 0.008 | 0.050 | 0.034 | 0.194 |
| SIM/CEM4 | 0.584 | 3.398 | 0.038 | 0.216 |

In summarizing the results shown in Table 4, demonstrated is that a conjugate according to the present invention not only retains substantial biological activity comprising antiviral activity against HIV (as compared to synthetic peptide alone), but surprisingly, in some cases, shows more antiviral potency than synthetic peptide alone.

Using the methods taught in Example 1 herein, additional conjugates were produced by varying the polymer, the terminus of the synthetic peptide which is operably bound to polymer, and the reactive functionality used for operably binding synthetic peptide to polymer. Two molecules of synthetic peptide (e.g. SEQ ID NO:4) were operably bound to polymer. Such conjugates were then tested for antiviral activity against HIV isolates IIIB, and HIV-1 T20S & HIV-1 T20R (see Table 2 for HIV resistant strains), with the antiviral activity (IC50) expressed in µg/ml The results for the various conjugates (Table 5, A-Q ), terminus of synthetic peptide used for operably binding polymer (Table 5, C-terminus denoted as "C", N-terminus denoted as "N") or if an internal lysine was used (Table 5, "Lys 18", signifying lysine as amino acid residue 18 in the amino acid sequence of the synthetic peptide), antiviral activity (IC50) against HIV-1 strain IIIB (Table 5, "IIIB"), antiviral activity (IC50) against HIV-1 T20S (Table 5, "T20S") and antiviral activity (IC50) against HIV-1 T20R (Table 5, "T20R"), are illustrated in Table 5.

Also for Table 5, the number following "PEG" refers to the number of ethylene units comprising the PEG (multiple numbers correspond multiple PEG units each of discrete species being operably bound together); alkyl with a number following it refers to an alkyl chain with the number referring to the number of carbon atoms comprising the alkyl chain; GLY refers to the amino acid glycine which was used as a linker between the polymer and the synthetic peptide; and AT refers to a triacid (e.g., trisuccinimidylamino triacetate).

TABLE 5

| Tested | Terminus | Polymer | IIIB | T20S | T20R |
|---|---|---|---|---|---|
| synthetic peptide alone | None | None | .007 | .010 | 1.2 |
| A | N | PEG 6 | .037 | .029 | .050 |
| B | C | PEG 6 | .117 | .053 | .070 |
| C | C | PEG 6 | .065 | .046 | .050 |
| D | N | alkyl C5 | .039 | .036 | .049 |
| E | N | PEG 8 | .018 | .026 | .020 |
| F | N | alkyl C8 | .089 | .049 | .087 |
| G | N | alkyl C11 | .174 | .176 | .218 |
| H | N | AT | .046 | .047 | .124 |
| I | N | PEG 4-6-4 | .029 | .012 | .029 |
| J | N | PEG 3 | .036 | .028 | .049 |
| K | N | PEG 4 | .033 | .026 | .067 |
| L | C | GLY-PEG 3 | .107 | .061 | .066 |
| M | C | GLY-C2 | .139 | .085 | .114 |
| N | N | PEG 10 | .039 | .017 | .023 |
| O | C | GLY-C6 | .140 | .083 | .044 |
| P | C | GLY-PEG 6 | .088 | .031 | .051 |
| Q | Lys 18 | PEG 6 | .057 | .055 | .120 |

In summarizing the results shown in Table 5, demonstrated are various illustrations of conjugates according to the present invention, each of which not only retains substantial biological activity comprising antiviral activity against HIV-1 (as compared to synthetic peptide alone), but unexpectedly also show durability against HIV resistant isolates, as compared to synthetic peptide alone.

EXAMPLE 4

In another illustrative embodiment, a conjugate according to the present invention was produced by operably binding two molecules of SEQ ID NO:114 via the N-terminus of the synthetic peptide to reactive functionalities of a polymer, PEG. More particularly, a molecule of SEQ ID NO:114 was operably bound to an acid of PEG, whereas another molecule of SEQ ID NO:114 was operably bound to a second acid of the PEG molecule in forming a conjugate comprising SEQ ID NO:114-PEG dimer. For example, PEG-6 diacid (5.4 mg, 0.016 mmole), and O-(1H-6-chlorobenzotriazole-1-yl)-N,N,N',N'-tetramethyluronium tetrafluoroborate (TCTU, 11.4 mg, 0.032 mmole) were dissolved in 1.5 ml 2:1 DCM:DMF (dichloromethane:dimethylformamide). N,N-diisopropylethylamine (DIEA, 11.1 µml, 0.064 mmole) was added, followed immediately by side-chain protected H(hydrogen)-SEQ ID NO:114 (250 mg, 0.032 mmole). The solution was stirred at ambient temperature for 4 hours. The DCM was removed by rotary evaporation, and then water (5 ml) was added to precipitate the peptide. The solid was collected by vacuum filtration, washed with water (3×5 ml) and dried to give the side-chain protected SEQ ID NO:114-PEG-6 dimer (225 mg) in 90% yield. The side-chain protected SEQ ID NO:114-PEG-6 dimer (225 mg) was dissolved in trifluoroacetic acid (TFA, 4.5 ml) containing water (0.25 ml) and dithiothreitol (DTT, 0.25 g) as cation scavengers. The solution was stirred at ambient temperature for 6 hours. To precipitate the crude SEQ ID NO:114-PEG-6 dimer, methyl tert-butyl ether (MTBE) was added. The solvent was decanted and the solid was washed several times with MTBE, then filtered and air-dried. The solid was dissolved in 10 ml of 1:1 water:acetonitrile and the pH was adjusted to 6-7 with dilute ammonium hydroxide. The pH of the solution was lowered to between 4 and 5 by adding acetic acid (0.2 ml). The resulting clear solution was allowed to stir at ambient temperature overnight to complete the side-chain deprotection. The solution was frozen, and then lyophilized to yield crude SEQ ID NO:114-PEG-6 dimer (150 mg). The crude SEQ ID NO:114-PEG-6 dimer was purified by high performance liquid chromatography (HPLC) using C18, 5 micron reverse phase packing as the stationary phase and acetonitrile/water with 0.1% TFA as the mobile phase (40-70% organic over 90 minutes). The pure product-containing fractions were pooled, frozen and lyophilized to give 8 mg of conjugate according to the present invention (89.2% by HPLC, MS found 9268.43, calculated 9268.35).

Using the methods outlined in Example 3 herein for determining antiviral activity, an HIV-1 strain sensitive to the antiviral effect of a peptide comprising SEQ ID NO:114 (Table 6, "114-S") and an HIV-1 strain resistant to treatment with a peptide comprising SEQ ID NO:114 (Table 6, "114-R") were used in an in vitro infectivity assay in which the antiviral effect of a peptide comprising SEQ ID NO:114; Table 6, "synthetic peptide alone") was compared to a conjugate according to the present invention (e.g., conjugate comprising two molecules of SEQ ID NO:114 operably bound to PEG 6; Table 6, "conjugate"). The results, with the IC50 and IC90 expressed in µg/ml, are illustrated in Table 6.

TABLE 6

| | Agent tested | | | |
|---|---|---|---|---|
| | 114-S: | | 114-R: | |
| | IC50 | IC90 | IC50 | IC90 |
| synthetic peptide alone | 0.005 | 0.034 | 2.40 | >20 |
| Conjugate | 0.016 | 0.169 | 0.15 | 12.46 |

In summarizing the results shown in Table 6, demonstrated is the unexpected result that a conjugate according to the present invention not only retains substantial biological activity comprising antiviral activity against HIV (as compared to synthetic peptide alone), but surprisingly shows durability comprising potent antiviral activity against HIV isolates which are resistant to synthetic peptide alone. Additionally, the conjugate illustrated in this example confirms the common property among synthetic peptides derived from either the HR1 region or the HR2 region of HIV-1 gp41 in being useful in producing a conjugate according to the present invention.

EXAMPLE 5

The present invention provides for conjugates which possess antiviral activity as evidenced by their ability to inhibit transmission of HIV to a target cell; and a method for inhibiting transmission of HIV to a target cell, comprising adding to the virus and cell an amount of conjugate according to the present invention effective to inhibit infection of the cell by HIV, and more preferably, to inhibit fusion between the virus and the target cell. This method may be used to treat HIV-infected individuals (therapeutically) or to treat individuals newly exposed to or at high risk of exposure (e.g., through drug usage or high risk sexual behavior) to HIV (prophylactically). Thus, for example, in the case of an HIV-1 infected individual, an effective amount of conjugate would be a dose sufficient (by itself and/or in conjunction with a regimen of doses) to reduce HIV viral load in the individual being treated. As known to those skilled in the art, there are several standard methods for measuring HIV viral load which include, but are not limited to, by quantitative cultures of peripheral blood mononuclear cells and by plasma HIV RNA measurements. The conjugates of the invention can be administered in a single administration, intermittently, periodically, or continuously, as can be determined by a medical practitioner, such as by monitoring viral load. Depending on the formulation containing conjugate, and such factors as the compositions of the polymer and synthetic peptide used in forming the conjugate and whether or not further comprising a pharmaceutically acceptable carrier and the nature of the pharmaceutically acceptable carrier, the conjugate according to the present invention may be administered with a periodicity ranging from days to weeks or possibly longer. Further, a conjugate according to the present invention may show synergistic results, of inhibiting transmission of HIV to a target cell, when used in combination (e.g., when used simultaneously, or in a cycling on with one drug and cycling off with another) with other antiviral drugs used for treatment of HIV (e.g., including, but not limited to, other HIV entry inhibitors (e.g., CCR5 inhibitors, retrocyclin, and the like), HIV integrase inhibitors, reverse transcriptase inhibitors (e.g., nucleoside or nonnucleoside), protease inhibitors, and the like, as well known in the art).

Effective dosages of a conjugate of the invention to be administered may be determined through procedures well known to those in the art; e.g., by determining potency, biological half-life, bioavailability, and toxicity. In a preferred embodiment, an effective conjugate dosage range is determined by one skilled in the art using data from routine in vitro and in vivo studies well know to those skilled in the art. For example, in vitro infectivity assays of antiviral activity, such as described herein, enables one skilled in the art to determine the mean inhibitory concentration (IC) of the conjugate necessary to block some amount of viral infectivity (e.g., 50% inhibition, $IC_{50}$; or 90% inhibition, $IC_{90}$). Appropriate doses can then be selected by one skilled in the art using pharmacokinetic data from one or more standard animal models, so that a minimum plasma concentration (C[min]) of the conjugate is obtained which is equal to or exceeds a predetermined IC value. While dosage ranges typically depend on the route of administration chosen and the formulation of the dosage, an exemplary dosage range of the conjugate according to the present invention may range from no less than 0.1 µg/kg body weight and no more than 10 mg/kg body weight; preferably a dosage range of from about 0.1-100 µg/kg body weight; and more preferably, a dosage of between from about 10 mg to about 250 mg of conjugate.

A conjugate of the present invention may be administered to an individual by any means that enables the active agent to reach the target cells (cells that can be infected by HIV). Thus, the conjugates of this invention may be administered by any suitable technique, including oral, parenteral (e.g., intramuscular, intraperitoneal, intravenous, or subcutaneous injection or infusion, intradermal, or implant), nasal, pulmonary, vaginal, rectal, sublingual, or topical routes of administration, and can be formulated in dosage forms appropriate for each route of administration. The specific route of administration will depend, e.g., on the medical history of the individual, including any perceived or anticipated side effects from such administration, and the formulation of conjugate being administered (e.g., the nature of the polymer and synthetic peptide of which the conjugate comprises). Most preferably, the administration is by injection (using, e.g., intravenous or subcutaneous means), but could also be by continuous infusion (using, e.g., slow-release devices or minipumps such as osmotic pumps, and the like). A conjugate according to the present invention may further comprise one or more pharmaceutically acceptable carrier; and may further depend on the formulation desired, site of delivery, the method of administration, the scheduling of administration, and other factors known to medical practitioners. Additionally, a conjugate may comprise nucleotide sequences encoding polymer and synthetic peptide, as described herein in more detail, which upon administration, is expressed in cells of interest using techniques and expression vectors well known in the art.

EXAMPLE 6

It is apparent to one skilled in the art from the descriptions herein, that where the polymer used in producing a conjugate according to the present invention is polyamino acid-based, that polynucleotides encoding such conjugate may be synthesized or constructed, and that such conjugate may be produced by recombinant DNA technology as a means of manufacture and/or (for example, in vivo production) for a method of inhibiting transmission of HIV to a target cell. It is also apparent to one skilled in the art that more than one polynucleotide sequence can encode a conjugate according to the present invention, and that such polynucleotides may be synthesized on the basis of triplet codons known to encode the amino acids of the amino acid sequence of the conjugate, third base degeneracy, and selection of triplet codon usage preferred by the host cell (e.g., prokaryotic or eukaryotic, species, etc.) in which expression is desired, For example, a polymer may comprise polylysine, and lysine may be encoded by any one of the codons AAA, or AAG. In another example, a heteropolymer comprised of lysines and alanines may be used, with alanine being encoded by any one of the codons GCA, GCG, GCC, or GCU. In another example in which one molecule of synthetic peptide is linked to the amino terminus of the polymer and a second molecule of synthetic peptide is linked to the carboxy terminus of the polymer, it may be desired to have a flexible linker which operably binds the molecules of synthetic peptide to the polymer. It is well known in the art that a flexible linker which may be applied to operably bind together two amino acid sequences may be comprised of glycine or glycine combined with other amino acids such as serine. Glycine is known to be encoded by any one or more of GGU, GGC, GGA, or GGG; whereas serine is known to be encoded by any one or more of AGU, AGC, UCU, UCC, UCA, or UCG. Illustrative examples may include, but are not limited to, (the number indicating the number of molecules): Gly(3), GlySerGly, Gly(4)Ser(3), GlySer, and the like. A preferred flexible linker may be determined using methods standard in the art. Thus, for example, a conjugate may comprise:

synthetic peptide-flexible linker-polymer-flexible linker-synthetic peptide.

For purposes of illustration only, and not limitation, examples of polynucleotides encoding synthetic peptide which may be applied to the conjugate according to the present invention comprise SEQ ID NOs:100-106 for synthetic peptides comprising SEQ ID NOs:63,65,66,61,62,4, &5 respectively); however, it is understood that different codons can be substituted which code for the same amino acid(s) as the original codons. Further, based on a preferred codon usage illustrated herein, one skilled in the art may easily determine codon usage for a synthetic peptide of similar sequence and/or origin (e.g., derived from HR1 or HR2 regions, such as, but not limited to, SEQ ID NOs: 3, 6-60, 64, and 67-99). In continuing this example, SEQ ID NOs:107-113 encode the same respective synthetic peptides as SEQ ID NOs:100-106. However, SEQ ID NOs:100-106 represent polynucleotides containing codon usage preferably for bacterial expression, whereas SEQ ID NOs:107-113 represent polynucleotides containing codon usage preferably for expression in mammalian expression systems.

In one embodiment, provided is a prokaryotic expression vector containing a polynucleotide encoding a conjugate according to the present invention, and its use for the recombinant production of conjugate. In one example, the polynucleotide may be positioned in a prokaryotic expression vector so that when conjugate is produced in bacterial host cells, it is produced as a fusion protein with sequences which assist in purification of the conjugate. For example, there are sequences known to those skilled in the art which, as part of a fusion protein with a polypeptide desired to be expressed, facilitates production in inclusion bodies found in the cytoplasm of the prokaryotic cell used for expression (see. e.g., Tokatlidis et al., 1993, *Protein Eng.* 6:947-952). The inclusion bodies may be separated from other prokaryotic cellular components by methods known in the art to include denaturing agents, and fractionation (e.g., centrifugation, column chromatography, and the like). In another example, there are commercially available vectors into which is inserted a desired nucleic acid sequence of interest to be expressed as a protein or peptide such that upon expression, the gene product also contains a plurality of terminal histidine residues ("His tags") that can be utilized in the purification of the gene product using methods standard in the art.

It is apparent to one skilled in the art that a nucleic acid sequence encoding a conjugate according to the present invention can be inserted into a plasmid or vectors other than plasmids, and other expression systems can be used including, but not limited to, bacteria transformed with a bacteriophage vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc.). Successful expression of the conjugate requires that either the recombinant DNA molecule comprising the encoding sequence of the conjugate, or the vector itself, contain the necessary control elements for transcription and translation which is compatible with, and recognized by the particular host system used for expression. Using methods known in the art of molecular biology, including methods described above, various promoters and enhancers can be incorporated into the vector or the recombinant DNA molecule comprising the encoding sequence to increase the expression of the conjugate, provided that the increased expression of the conjugate is compatible with (for example, non-toxic to) the particular host cell system used. As apparent to one skilled in the art, the selection of the promoter will depend on the expression system used. Promoters vary in strength, i.e., ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising *E. coli* include the lac promoter, trp promoter, recA promoter, ribosomal RNA promoter, the $P_R$ and $P_L$ promoters, lacUV5, ompF, bla, lpp, and the like, may be used to provide transcription of the inserted nucleotide sequence encoding the synthetic peptide. Commonly used mammalian promoters in expression vectors for mammalian expression systems are the promoters from mammalian viral genes. Examples include the SV40 early promoter, mouse mammary tumor virus LTR promoter, adenovirus major late promoter, *herpes simplex* virus promoter, and the CMV promoter.

In the case where expression of the conjugate may be lethal or detrimental to the host cells, the host cell strain/line and expression vectors may be chosen such that the action of the promoter is inhibited until specifically induced. For example, in certain operons the addition of specific inducers is necessary for efficient transcription of the inserted DNA (e.g., the lac operon is induced by the addition of lactose or isopropylthio-beta-D-galactoside; trp operon is induced when tryptophan is absent in the growth media; and tetracycline can be use in mammalian expression vectors having a tet sensitive promoter). Thus, expression of the conjugate may be controlled by culturing transformed or transfected cells under conditions such that the promoter controlling the expression from the encoding sequence is not induced, and when the cells reach a suitable density in the growth medium, the promoter can be induced for expression from the encoding sequence. Other control elements for efficient gene transcription or message translation are well known in the art to include enhancers, transcription or translation initiation signals, transcription termination and polyadenylation sequences, and the like.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept; and thus, such modifications and/or adaptations are intended to be within the meaning and scope of the appended claims.

What is claimed is:

1. A peptide-polymer conjugate comprising a polymer to which is covalently attached two or more synthetic peptides derived from the Human Immunodeficiency Virus (HIV) gp41 heptad repeat region one (HR1), two (HR2), or a combination thereof, wherein said HR1 peptides consist of an amino acid sequence between 16 and 60 amino acids and said HR2 peptides consist of an amino acid sequence between 16 and 64 amino acids, and wherein the conjugate has greater antiviral activity against resistant HIV-1 strains as compared to the unconjugated peptide alone.

2. The conjugate according to claim 1, wherein the polymer comprises a molecular weight in a range of molecular weights of from about 200 daltons to about 20,000 daltons.

3. The conjugate according to claim 2, wherein the polymer comprises polyethylene glycol comprising a specific number of ethylene units.

4. The conjugate according to claim 1, wherein each synthetic peptide of the conjugate comprises an amino acid sequence derived from the HR1 region of HIV gp41.

5. The conjugate according to claim 4, wherein each synthetic peptide of the conjugate comprises an identical amino acid sequence.

6. The conjugate according to claim 1, wherein each synthetic peptide of the conjugate comprises an amino acid sequence derived from the HR2 region of HIV gp41.

7. The conjugate according to claim 6, wherein each synthetic peptide of the conjugate comprises an identical amino acid sequence.

8. The conjugate according to claim 1, wherein at least one molecule of synthetic peptide of the conjugate comprises an amino acid sequence derived from the HR1 region of HIV gp41, and wherein at least one molecule of synthetic peptide of the conjugate comprises an amino acid sequence derived from the HR2 region of HIV gp41.

9. The conjugate according to claim 1, wherein the synthetic peptides are covalently attached to the polymer via a portion of each synthetic peptide selected from the group consisting of an N-terminus, a C-terminus, and an internal lysine.

* * * * *